US005576421A

United States Patent [19]

Saito et al.

[11] Patent Number: 5,576,421

[45] Date of Patent: Nov. 19, 1996

[54] RECOMBINANT CHIMERIC HIV-1 GAG-ENV FUSION PROTEINS

[75] Inventors: Atsushi Saito, Kagawa-ken; Hideo Sinagawa, Suita; Atsuo Nakata, Toyonaka, all of Japan

[73] Assignee: The Research Foundation for Microbial Diseases of Osaka University, Osaka, Japan

[21] Appl. No.: 375,510

[22] Filed: Jan. 18, 1995

Related U.S. Application Data

[63] Continuation of Ser. No. 985,949, Dec. 4, 1992, abandoned.

[30] Foreign Application Priority Data

Jun. 4, 1992 [JP] Japan .................................... 4-170270

[51] Int. Cl.[6] ............................ C07K 1/00; C07K 14/00; C07K 17/00; A61K 39/21

[52] U.S. Cl. .................. 530/350; 424/188.1; 424/192.1; 435/7.1; 435/172.3; 435/974

[58] Field of Search ............................. 424/188.1, 192.1, 424/208.1; 435/7.1, 69.1, 69.3, 172.3, 974; 530/350

[56] References Cited

U.S. PATENT DOCUMENTS 4,925,784 5/1990 Crowl et al. ................................ 435/5

FOREIGN PATENT DOCUMENTS 0227169 7/1987 European Pat. Off. ....... G01N 33/68
0307149 3/1989 European Pat. Off. ..... G01N 33/543
0343132 11/1989 European Pat. Off. ........ C12N 15/00
0340837 11/1989 European Pat. Off. ....... A61K 39/21
0370458 5/1990 European Pat. Off. ........ C07K 13/00
0449116 10/1991 European Pat. Off. ........ C12N 15/48
1179687 7/1989 Japan .
62336292 7/1989 Japan .
2188639 10/1987 United Kingdom ........... C12N 15/00

OTHER PUBLICATIONS

Shoeman, et al, 1987, "Comparison of recombinant human immunodeficiency . . . " Analytical Biochem. 161:370–379.

Siitari et al. (1990) *Journal of Clinical Microbiology* 28(9):2022–2029.

Ellinger, et al., Virology (1991), 180(2):811–813.

*Primary Examiner*—Robert D. Budens
*Assistant Examiner*—Jeffrey S. Parkin
*Attorney, Agent, or Firm*—Birch, Stewart, Kolasch & Birch, LLP

[57] ABSTRACT

Disclosed is the construction, expression, and purification of chimeric human immunodeficiency virus type 1 (HIV-1) Gag-Env fusion proteins. Gag-Env chimeras were generated by fusing the amino terminus (amino acids 512–611) of the Env protein to the carboxyl terminus of the Gag protein (either amino acids 121–406 or 308–406). These proteins were overexpressed in *Escherichia coli*, purified, and their immunologic properties ascertained. Both chimeric proteins displayed immunoreactivity towards antisera obtained from HIV-1 seropositive patients. These HIV-1 Gag-Env fusion proteins should provide useful antigens for the detection of HIV-1-specific antibodies.

3 Claims, 5 Drawing Sheets

FIG. 1 —(1)

10 20
MetGlyAlaArgAlaSerValLeuSerGlyGlyGluLeuAspLysTrpGluLysIleArg 30 40
LeuArgProGlyGlyLysLysGlnTyrLysLeuLysHisIleValTrpAlaSerArgGlu 50 60
LeuGluArgPheAlaValAsnProGlyLeuLeuGluThrSerGluGlyCysArgGlnIle 70 80
LeuGlyGlnLeuGlnProSerLeuGlnThrGlySerGluGluLeuArgSerLeuTyrAsn 90 100
ThrIleAlaValLeuTyrCysValHisGlnArgIleAspValLysAspThrLysGluAla 110 120
LeuAspLysIleGluGluGluGlnAsnLysSerLysLysLysAlaGlnGlnAlaAlaAla 130 140
AspThrGlyAsnAsnSerGlnValSerGlnAsnTyrProIleValGlnAsnLeuGlnGly 150 160
GlnMetValHisGlnAlaIleSerProArgThrLeuAsnAlaTrpValLysValValGlu 170 180
GluLysAlaPheSerProGluValIleProMetPheSerAlaLeuSerGluGlyAlaThr 190 200
ProGlnAspLeuAsnThrMetLeuAsnThrValGlyGlyHisGlnAlaAlaMetGlnMet 210 220
LeuLysGluThrIleAsnGluGluAlaAlaGluTrpAspArgLeuHisProValHisAla 230 240
GlyProIleAlaProGlyGlnMetArgGluProArgGlySerAspIleAlaGlyThrThr 250 260
SerThrLeuGlnGluGlnIleGlyTrpMetThrHisAsnProProIleProValGlyGlu 270 280
IleTyrLysArgTrpIleIleLeuGlyLeuAsnLysIleValArgMetTyrSerProThr 290 300
SerIleLeuAspIleArgGlnGlyProLysGluProPheArgAspTyrValAspArgPhe 310 320
TyrLysThrLeuArgAlaGluGlnAlaSerGlnGluValLysAsnTrpMetThrGluThr 330 340
LeuLeuValGlnAsnAlaAsnProAspCysLysThrIleLeuLysAlaLeuGlyProGly 350 360
AlaThrLeuGluGluMetMetThrAlaCysGlnGlyValGlyGlyProGlyHisLysAla

FIG. 1 –(2)

370 380
ArgValLeuAlaGluAlaMetSerGlnValThrAsnProAlaThrIleMetIleGlnLys 390 400
GlyAsnPheArgAsnGlnArgLysThrValLysCysPheAsnCysGlyLysGluGlyHis 410 420
IleAlaLysAsnCysArgAlaProArgLysLysGlyCysTrpLysCysGlyLysGluGly 430 440
HisGlnMetLysAspCysThrGluArgGlnAlaAsnPheLeuGlyLysIleTrpProSer 450 460
HisLysGlyArgProGlyAsnPheLeuGlnSerArgProGluProThrAlaProProGlu 470 480
GluSerPheArgPheGlyGluGluThrThrThrProSerGlnLysGlnGluProIleAsp 490 500
LysGluLeuTyrProLeuAlaSerLeuArgSerLeuPheGlySerAspProSerSerGln

FIG. 2-(1)

10 20
SerAlaThrGluLysLeuTrpValThrValTyrTyrGlyValProValTrpLysGluAla 30 40
ThrThrThrLeuPheCysAlaSerAspAlaLysAlaTyrAspThrGluValHisAsnVal 50 60
TrpAlaThrHisAlaCysValProThrAspProAsnProGlnGluValValLeuValAsn 70 80
ValThrGluAsnPheAsnMetTrpLysAsnAspMetValGluGlnMetHisGluAspIle 90 100
IleSerLeuTrpAspGlnSerLeuLysProCysValLysLeuThrProLeuCysValSer 110 120
LeuLysCysThrAspLeuLysAsnAspThrAsnThrAsnSerSerSerGlyArgMetIle 130 140
MetGluLysGlyGluIleLysAsnCysSerPheAsnIleSerThrSerIleArgAspLys 150 160
ValGlnLysGluTyrAlaPhePheTyrLysLeuAspIleValProIleAspAsnThrSer 170 180
TyrArgLeuIleSerCysAsnThrSerValIleThrGlnAlaCysProLysValSerPhe 190 200
GluProIleProIleHisTyrCysAlaProAlaGlyPheAlaIleLeuLysCysAsnAsn 210 220
LysThrPheAsnGlyThrGlyProCysThrAsnValSerThrValGlnCysThrHisGly 230 240
IleArgProValValSerThrGlnLeuLeuLeuAsnGlySerLeuAlaGluGluAspVal 250 260
ValIleArgSerAlaAsnPheThrAspAsnAlaLysThrIleIleValGlnLeuAsnThr 270 280
SerValGluIleAsnCysThrArgProAsnAsnAsnThrArgLysSerIleArgIleGln 290 300
ArgGlyProGlyArgAlaPheValThrIleGlyLysIleGlyAsnMetArgGlnAlaHis 310 320
CysAsnIleSerArgAlaLysTrpAsnAlaThrLeuLysGlnIleAlaSerLysLeuArg 330 340
GluGlnPheGlyAsnAsnLysThrIleIlePheLysGlnSerSerGlyGlyAspProGlu 350 360
IleValThrHisSerPheAsnCysGlyGlyGluPhePheTyrCysAsnSerThrGlnLeu

FIG. 2 —(2)

370 380
PheAsnSerThrTrpPheAsnSerThrTrpSerThrGluGlySerAsnAsnThrGluGly 390 400
SerAspThrIleThrLeuProCysArgIleLysGlnPheIleAsnMetTrpGlnGluVal 410 420
GlyLysAlaMetTyrAlaProProIleSerGlyGlnIleArgCysSerSerAsnIleThr 430 440
GlyLeuLeuLeuThrArgAspGlyGlyAsnAsnAsnAsnGlySerGluIlePheArgPro 450 460
GlyGlyGlyAspMetArgAspAsnTrpArgSerGluLeuTyrLysTyrLysValValLys 470 480
IleGluProLeuGlyValAlaProThrLysAlaLysArgArgValValGlnArgGluLys 490 500
ArgAlaValGlyIleGlyAlaLeuPheLeuGlyPheLeuGlyAlaAlaGlySerThrMet 510 520
GlyCysThrSerMetThrLeuThrValGlnAlaArgGlnLeuLeuSerAspIleValGln 530 540
GlnGlnAsnAsnLeuLeuArgAlaIleGluAlaGlnGlnHisLeuLeuGlnLeuThrVal 550 560
TrpGlyIleLysGlnLeuGlnAlaArgIleLeuAlaValGluArgTyrLeuLysAspGln 570 580
GlnLeuLeuGlyIleTrpGlyCysSerGlyLysLeuIleCysThrThrAlaValProTrp 590 600
AsnAlaSerTrpSerAsnLysSerLeuGluGlnIleTrpAsnAsnMetThrTrpMetGlu 610 620
TrpAspArgGluIleAsnAsnTyrThrSerLeuIleHisSerLeuIleGluGluSerGln 630 640
AsnGlnGlnGluLysAsnGluGlnGluLeuLeuGluLeuAspLysTrpAlaSerLeuTrp 650 660
AsnTrpPheAsnIleThrAsnTrpLeuTrpTyrIleLysLeuPheIleMetIleValGly 670 680
GlyLeuValGlyLeuArgIleValPheAlaValLeuSerIleValAsnArgValArgGln 690 700
GlyTyrSerProLeuSerPheGlnThrHisLeuProIleProArgGlyProAspArgPro 710 720
GluGlyIleGluGluGluGlyGlyGluArgAspArgAspArgSerIleArgLeuValAsn

FIG. 2—(3)

```
                         730                 740
GlySerLeuAlaLeuIleTrpAspAspLeuArgSerLeuCysLeuPheSerTyrHisArg

                         750                 760
LeuArgAspLeuLeuLeuIleValThrArgIleValGluLeuLeuGlyArgArgGlyTrp

                         770                 780
GluAlaLeuLysTyrTrpTrpAsnLeuLeuGlnTyrTrpSerGlnGluLeuLysAsnSer

                         790                 800
AlaValAsnLeuLeuAsnAlaThrAlaIleAlaValAlaGluGlyThrAspArgValIle

                         810                 820
GluValLeuGlnAlaAlaTyrArgAlaIleArgHisIleProArgArgIleArgGlnGly

LeuGluArgIleLeuLeu
```

RECOMBINANT CHIMERIC HIV-1 GAG-ENV FUSION PROTEINS

This application is a continuation of application Ser. No. 07/985,949 filed on Dec. 4, 1992, now abandoned.

BACKGROUND OF THE INVENTION

1. Field of the Invention

The present invention relates to a human imunodeficiency virus (HIV) antigen. More particularly, the present invention is concerned with a substantially pure HIV antigen comprising a Gag-Env fusion protein consisting of a specific Gag peptide fused at its C-terminus to a specific Env peptide, which antigen not only exhibits excellent HIV antigenicity, but which can also be obtained at a level that has never been attained to date, and is also concerned with a method for producing the same. The HIV antigen of the present invention is useful as an active component for a diagnostic reagent, a vaccine, an antibody preparation and a therapeutic reagent for AIDS (acquired immune deficiency syndrome).

2. Discussion of Related Art

As is well know in the art, since the first AIDS patient was reported in 1981, the number of AIDS patients has been increasing in geometric progression. As of April 1992, the total number of AIDS patients is as large as about 500,000. Although research on the prevention and medical treatment of the disease have been extensively and intensively made throughout the world, no infallible preventive and therapeutic methods are in practical use. The global spread of AIDS without any infallible preventive and therapeutic methods is now a world-wide problem. On the other hand, the AIDS virus was first isolated and identified in 1983, and since then, research on AIDS in both the basic and clinical aspects has become active in the field of virology (see *Nature*, 326, 435–436, 1987). As a result, remarkable progress has been made in the diagnosis of AIDS, and immunodiagnostic reagents for use in the diagnosis and methods for producing the same are rapidly being improved. AIDS viruses have been isolated from humans, monkeys and cats. Of them, the virus isolated from humans is designated "human immunodeficiency virus (HIV)". HIV is broadly classified into HIV-1 and HIV-2. HIV-1 is spreading worldwide, i.e., in the U.S.A., Europe, Central Africa and other numerous countries of the world, while HIV-2 is mainly spreading only in West Africa. HIV is a spherical virus of from 100 to 140 nm in diameter which has an envelope (Env). The Env is comprised of transmembrane protein (gp41) and 70 to 80 peplomers (gp120) which form rod-shaped protrusions, each having a diameter of 15 nm and a height of about 9 nm, and which are present in the surface of the vital particle. In the core of the viral particle, two single strand RNA molecules of the viral genome form a complex with reverse transcriptase and structural proteins as the viral core, in which primer tRNA is present. The viral genome has a length of more than 9 kb and is comprised of about 10 different genes. Essentially, the viral genome is comprised of the following three major genes coding for the viral components essential for multiplication of the virus:

(1) gag (group-specific antigen) gene coding for p55 which is a precursor protein of three types of structural proteins p17, p24, and p15 of the viral core;

(2) pol (polymerase) gene coding for a precursor of three different enzymes, i.e., protease, reverse transcriptase, and integrase; and (3) env (envelope) gene coding for gp160, which is a precursor of two types of glycoproteins, gp120 and gp41 forming the vital envelope.

These genes are arranged in the sequence of gag. pol . . . env in the direction from the 5'-end toward the 3'-end of the viral genome.

The remaining approximately seven other genes, so-called accessory genes, are believed to take part in the control of infection, multiplication, maturation of HIV, and the development of illness.

Various HIV antigens and enzymes essential for the basic studies of AIDS and for the development and production of therapeutic reagents, diagnostics and vaccines therefor can be produced by culturing HIV. However, the culturing of HIV is accompanied by the danger of fatal biohazard. Therefore, various studies and attempts have been made to develop a technique for the production of such antigens and enzymes in large quantity without culturing HIV. For example, with respect to both the gag and pol genes, various HIV antigens and enzymes, such as Gag proteins p17, p24, and p15 (see Japanese Patent Application Laid-Open Specification No. 4-117289) and pol gene products, e.g., protease, reverse transcriptase, and integrase (see Japanese Patent Application Laid-Open Specification No. 2-265481), have been successfully produced in high yield by a technique capable of expressing the genes in *E. coli* and processing the produced protein, and some of the antigens and enzymes have been put to practical use.

On the other hand, with respect to the expression of the env gene of HIV, the highly efficient expression of the env gene alone is extremely difficult, as compared to that of the gag and pol genes, although the reason has not yet been elucidated. Therefore, in many cases, the env gene of HIV is expressed in a chimeric form with a foreign gene, thereby producing the Env peptide as a protein in which the Env peptide is fused to a foreign peptide. For example, it is known to express the env gene in a chimeric form with a poliovirus gene, to thereby produce a fusion protein in which the Env peptide is fused to a poliovirus antigen peptide (see *Journal of Virology*, 65, 2875–2883, 1991). It is also known to express the env gene in a chimeric form with a gag gene by means of *E. coli* expression plasmid pEV-vrf, to thereby produce a Gag-Env fusion protein in which the Env peptide is fused to the Gag peptide (*Analytical Biochemistry*, 161, 370–379, 1987). In these cases, a peptide coded for by a foreign gene or a structural gene, which is positioned downstream of a promotor in an expression plasmid, is fused at its C-terminus to the Env peptide. When the Env peptide is fused to a foreign peptide, the Env peptide is likely to exhibit non-specificity in a reaction with test serum. Therefore, the Env peptide which is fused to a foreign peptide is inferior to a pure HIV antigen in quality and reliability for use as an HIV antigen. Furthermore, the Env peptide which is fused to a foreign peptide is not good in terms of production yield.

It is conceivable to cleave a fusion protein at the site of the junction of the Env peptide and a foreign peptide, in order to remove the foreign peptide. However, by this method, it is not possible to obtain the desired Env peptide in a foreign peptide-free, pure form in high yield and at low cost.

On the other hand, it is known to express the Env peptide as a Gag-Env fusion protein consisting of a Gag peptide fused to the Env peptide (see Japanese Patent Application Laid-Open Specification No. 1-179687; *Virology*, 180, 811–813, 1991 and European Patent Application Publication No. 307149). However, the yield of the conventional Gag-Env fusion protein is likely to be poor, thereby causing the production cost to be high. Furthermore, such a Gag-Env fusion protein is likely to be poor in antigenicity, so that its reliability as an HIV antigen is low.

Thus, the conventional HIV antigens are disadvantageous in that they are poor in quality, reliability and productivity. Therefore, a novel HIV antigen which is free from such problems has been much desired from a practical and commercial viewpoint, and the development of such a novel HIV antigen has been a task of great urgency in the art.

As mentioned above, the Env peptide has conventionally been produced in relatively large quantity as a fusion protein in which the Env peptide is fused to a foreign peptide, but the conventionally obtained Env peptide as a fusion protein is likely to exhibit non-specificity in an antigen-antibody reaction, so that the fusion protein is unsatisfactory in quality and reliability for use as an HIV antigen. Such a fusion protein is unsuitable for the practical diagnosis of AIDS. It should further be noted that the present invention has been attained by overcoming the serious problem of the prior art that even when the gag gene and env gene are fused to each other and expressed by conventional genetic engineering techniques, a Gag-Env fusion protein which is highly reliable as an HIV antigen can never be produced in high yield.

SUMMARY OF THE INVENTION

The present inventors have made extensive and intensive studies with a view toward solving the above-mentioned problems by developing a novel HIV antigen. As a result, the present inventors have succeeded in developing a novel HIV antigen which is excellent in quality, reliability, and productivity, and hence is extremely advantageous from a practical and commercial viewpoint. Particularly, the present inventors have unexpectedly found that a specific, substantially pure HIV antigen comprising a Gag-Env fusion protein (wherein the Gag-Env fusion protein consists of a Gag peptide fused at its C-terminus to an Env peptide, and wherein the Gag peptide comprises a contiguous sequence of at least ten amino acids of the amino acid sequence represented by Gag (308-437) defined herein, and the Env peptide comprises at least a part of the amino acid sequence represented by Env (512-699) defined herein, the part containing at least one epitope which is reactive to an HIV antibody, not only exhibits excellent antigenicity, but can also be produced in a yield which is so high as has conventionally been unable to be attained.

Furthermore, in the process of designing the above-mentioned HIV antigen of the present invention comprising a specific Gag-Env fusion protein, the present inventors have unexpectedly found that as an HIV antigen, the Gag protein obtained by expressing the gag gene coding for the entire amino acid sequence of the Gag protein as an immature protein is advantageous in that it not only exhibits a broad spectrum of reactivity with HIV antibodies, but also exhibits strong reactivity in antigen-antibody reactions, as compared to the Gag proteins, p17, p24, and p15, which are mature proteins and have conventionally been known to be useful as antigens for use in the diagnosis of AIDS.

Based on these novel findings, the present invention has been completed.

Therefore, it is an object of the present invention to provide a substantially pure HIV antigen which is of high quality and which does not exhibit immunologically non-specific reactivity, and hence can be advantageously used for producing a testing reagent for HIV, an HIV antibody, a reagent for the diagnosis of AIDS, a vaccine for AIDS, and the like.

It is another object of the present invention to provide a method for producing an HIV antigen in high yield and with high efficiency.

It is still another object of the present invention to provide a recombinant DNA molecule which is useful for production of an HIV antigen in high yield and with high efficiency.

It is a further object of the present invention to provide a reagent for the diagnosis of AIDS.

It is still a further object of the present invention to provide a vaccine for AIDS.

The foregoing and other objects, features and advantages of the present invention will be apparent from the following detailed description and appended claims taken in connection with the accompanying drawings.

BRIEF DESCRIPTION OF THE DRAWINGS

In the accompanying drawings:

FIGS. 1-(1) through 1-(2) show the entire amino acid sequence of the Gag protein, SEQ. ID NO: 1, coded for by the entire region of the gag gene contained in plasmid pNL4-3 containing the entire HIV-1 genome; and FIGS. 2-(1) through 2-(3) show the entire amino acid sequence of the Env protein, SEQ. ID NO: 2, coded for by the entire region of the env gene contained in plasmid pNL4-3 containing the entire HIV-1 genome.

DETAILED DESCRIPTION OF THE INVENTION

In one aspect of the present invention, there is provided a substantially pure HIV antigen comprising a Gag-Env fusion protein, wherein the Gag-Env fusion protein consists of a Gag peptide fused at its C-terminus to an Env peptide.

In the HIV antigen of the present invention, the Gag peptide comprises a contiguous sequence of at least ten amino acids of the amino acid sequence represented by Gag (308-437), wherein each of the numbers indicated in the parentheses is the positional amino acid number in the entire amino acid sequence of the Gag protein shown in FIGS. 1-(1) through 1-(2). The Env peptide comprises at least a part of the amino acid sequence represented by Env (512-699), wherein the part contains at least one epitope which is reactive to an HIV antibody, and wherein each of the numbers indicated in the parentheses is the positional amino acid number in the entire amino acid sequence of the Env protein of HIV shown in FIGS. 2-(1) through 2-(3).

In the present invention, the region of the amino acid sequence of each of the various Gag peptides and the region of the amino acid sequence of each of the various Env peptides are indicated in parentheses as indicated above. With respect to the Gag peptide, each of the numbers indicated in the parentheses is the positional amino acid number in the entire amino acid sequence of the Gag protein of HIV shown in FIGS. 1-(1) through 1-(2) and, with respect to the Env peptide, each of the numbers indicated in the parentheses is the positional amino acid number in the entire amino acid sequence of the Env protein of HIV shown in FIGS. 2-(1) through 2-(3).

In the present invention, unless otherwise specified, the left end and right end of the amino acid sequence of the peptide or protein are the N-terminus and C-terminus, respectively. In the amino acid sequence, Asp represents an aspartic acid residue, Glu a glutamic acid residue, Lys a lysine residue, Arg an arginine residue, His a histidine residue, Asn an asparagine residue, Gln a glutamine residue, Ser a serine residue, Thr a threonine residue, Tyr a tyrosine residue, Cys a cysteine residue, Trp a tryptophan residue, Phe a phenylalanine residue, Gly a glycine residue, Ala an alanine residue, Val a valine residue, Leu a leucine residue, Ile an isoleucine residue, Pro a proline residue, and Met a methionine residue.

In the HIV antigen of the present invention comprising the above-defined Gag-Env fusion protein, it is preferred that the at least one epitope contained in the part of the Env peptide be a contiguous sequence of at least five amino acids of the amino acid sequence represented by Env (512-699).

In the present invention, the Gag peptide of the Gag-Env fusion protein comprises a contiguous sequence of at least ten amino acids of the amino acid sequence represented by Gag (308-437). The Gag peptide comprises a contiguous sequence of preferably at least 30 amino acids, more preferably at least 50 amino acids, still more preferably at least 70 amino acids of the amino acid sequence represented by Gag (308-437). Most preferably, the Gag peptide comprises an amino acid sequence represented by Gag (308-406) or Gag (308-437). In this connection, it should be noted that when the Gag peptide of the Gag-Env fusion protein contains an amino acid sequence positioned on the N-terminal side from the 307th amino acid of the entire amino acid sequence of the Gag protein and/or an amino acid sequence positioned on the C-terminal side from the 438th amino acid of the entire amino acid sequence of the Gag protein, the production yield of the Gag-Env fusion protein becomes disadvantageously lowered.

From the viewpoint of attaining improved antigenicity and productivity of the Gag-Env fusion protein, it is required that the Env peptide comprise at least a part of the amino acid sequence represented by Env (512-699), which part contains at least one epitope which is reactive to an HIV antibody. The epitope of the Env peptide comprises a contiguous sequence of preferably at least 5 amino acids, more preferably at least 10 amino acids, most preferably at least 15 amino acids of the amino acid sequence represented by Env (512-699).

The Gag-Env fusion protein of the HIV antigen of the present invention can be produced, using genetic engineering techniques, by a method which comprises ligating an env gene coding for the above-mentioned specific Env peptide containing at least one epitope of an HIV antigen to a gag gene coding for the above-mentioned specific Gag peptide downstream of the gag gene, to thereby obtain a recombinant DNA molecule comprising a gag-env fusion gene, and expressing the gag-env fusion gene. According to the present invention, by the expression of the above-mentioned specific gag-env fusion gene, a novel HIV antigen, which has excellent antigenicity and therefore is effective for detecting HIV antibodies with extremely high accuracy, has for the first time been produced. The HIV antigen of the present invention is also advantageous in that the antigen can be provided in a yield which is so high as has conventionally been unattainable.

The Gag-Env fusion protein of the HIV antigen of the present invention reacts with all of the sera from HIV carriers tested and, therefore, the Gag-Env fusion protein of the HIV antigen of the present invention is extremely useful not only as an antigen for producing a diagnostic reagent but also as an active ingredient for an HIV vaccine.

As mentioned above, there have been reported the usefulness of various types of partial peptides of the Gag protein (see, for example, Japanese Patent Application Laid-Open Specification No. 4-117289). However, the usefulness of the entire Gag protein (p55), i.e., the entire amino acid sequence thereof, has not yet been reported. The reason why the usefulness of Gag protein p55 has not yet been reported resides in the fact that p55 is an extremely unstable immature protein which is formed in the course of the formation of HIV particles, and usually immediately undergoes processing to differentiate into mature proteins p17, p24, and p15. Conventionally, it has been totally inconceivable to use such an immature protein as an HIV antigen. As shown in step 2 of Example 2 described later, the present inventors have produced p55, p17, p24, and p15 by recombinant DNA techniques, and made comparisons between p55, p17, p24, and p15 with respect to their reactivities with antibodies in sera derived from HIV carriers. As a result, it has surprisingly been found that, among these proteins, p55 has the highest reactivity with HIV antibodies, and that the minimum quantity of p55 necessary for detecting antibodies is smaller than those of the above-mentioned mature Gag proteins. That is, Gag protein p55, even alone, can be used as an effective antigen for diagnosis of AIDS. Furthermore, when Gag protein p55 is used in the form of a mixture with the above-mentioned Gag-Env fusion protein, the reliability of reactivity with HIV antibodies is enhanced.

Accordingly, in another aspect of the present invention, there is provided an HIV antigen, which comprises a mixture of the HIV antigen comprising the above-mentioned Gag-Env fusion protein and a Gag protein in substantially isolated form comprising the amino acid sequence represented by Gag (1-500), which is the entire amino acid sequence of the Gag protein shown in FIGS. 1-(1) through 1-(2), wherein each of the numbers indicated in the parentheses is the positional amino acid number in FIGS. 1-(1) through 1-(2).

Further, in still another aspect of the present invention, there is provided a substantially pure HIV antigen, comprising a Gag protein in substantially isolated form comprising the amino acid sequence represented by Gag (1-500), which is the entire amino acid sequence of the Gag protein shown in FIGS. 1-(1) through 1-(2), wherein each of the numbers indicated in the parentheses is the positional amino acid number in FIGS. 1-(1) through 1-(2).

The present invention is described below in more detail.

Essentially, the HIV antigens of the present invention can be prepared in accordance with the following schemes I to III.

Scheme I. Determination of a region of an Env protein having reactivity with HIV antibody:

Various env gene fragments are individually fused to a highly expressing gene, such as the lacZ gene, downstream thereof so that various regions of the env gene are individually expressed in a chimeric form with, e.g., the LacZ gene, thereby producing Env peptides as fusion proteins each comprised of a respective Env peptide and a LacZ protein (β-galactosidase). Then, these expression products are subjected to an immunological reaction with a large number of sera from AIDS patients, asymptomatic HIV carriers (AC), and AIDS-related complex (ARC) patients, thereby identifying the epitope region of the Env protein, which epitope region is defined to exhibit a strong, specific reactivity with the sera.

Scheme II. Production of a Gag-Env fusion protein in large quantity and confirmation of reactivity thereof with HIV antibodies:

With respect to various env gene fragments coding for the partial Env peptides containing epitope regions identified in scheme I, above, and to various gag gene fragments coding for Gag peptides, the following procedure is performed in order to identify a Gag-Env fusion protein which is desirable from the viewpoint of improving both productivity (yield) and antigenicity. Illustratively stated, with respect to various combinations of env gene fragments and gag gene fragments, an env gene fragment is fused to a gag gene downstream thereof, and, under the control of a promoter, the env gene is expressed in a chimeric form with the gag gene, thereby producing an Env peptide as a Gag-Env fusion protein.

With respect to the Gag-Env fusion protein which is produced in the largest quantity, the reactivity of the Gag-Env fusion protein with HIV antibodies is determined.

Scheme III. Confirmation of reactivity of Gag protein p55 having the entire amino acid sequence of a Gag protein:

In the same manner as in scheme II above, Gag protein p55 and Gag peptides p17, p24, and p15 are produced and individually subjected to an immunological reaction with sera from HIV carriers, and the reactivities of p55, p17, p24, and p15 with the sera are compared with one another, thereby confirming that p55 is the most active with respect to both reactivity and HIV detection ratio.

The techniques required for practicing the above-mentioned schemes I to III will now be described.

(1) Preparation of cDNA fragments containing the gag gene and/or env gene of HIV:

The entire region or a fragment of each of the gag gene and the env gene can be used. The entire region or fragment is inserted into a vector for high expression so that the reading frame of the insert matches with that of the vector. Since the HIV genome consists of RNA, when gene expression using recombinant DNA techniques is conducted, it is necessary that the above-mentioned HIV genes be converted to cDNA fragments complementary thereto. The cDNA fragments can be prepared from the provirus genome which is integrated into a chromosome of a host cell or from a cloned extrachromosomal circular DNA. Alternatively, the cDNA fragments can be screened from a cDNA library which has been constructed by a conventional method using reverse transcriptase, and using as a template the RNA genome extracted from virus particles of HIV. However, in the above-mentioned methods for the preparation of cDNA fragments, it is necessary to directly handle highly dangerous HIV. From the viewpoint of biohazard prevention, it is not preferable to directly handle HIV. Accordingly, in order to not only avoid the biohazard problems caused by HIV, but also to save labor in the preparation of cDNA fragments, it is recommended that known and established cDNA clones of HIV gene be used. With respect to operations for studying HIV genes, such as gene cloning, preparation of a restriction map and determination of nucleotide sequences, many reports have been issued by researchers around the world. For assuring safety and efficiency, it is desirable to utilize the results of these published studies. For example, use can be made of plasmids, such as pNL3-1, pNL3-2 and pNL4-3, all of which are genomic clones of HIV-1 provirus and available from the National Institutes of Health, U.S.A. (with respect to pNL3-1 and pNL3-2, see *Journal of Virology,* 59, 284–291, 1986; and with respect to pNL4-3, see GenBank data file HIVNL43). Further, using plasmid pNL4-3, microorganisms containing various plasmids carrying a partial region of the HIV-1 genome have been prepared and deposited. Illustratively stated, these deposited microorganisms are *E. coli* JM109/pCV91, containing plasmid pCV91 having a central region of a gag-pol fusion gene (deposited at the Fermentation Research Institute, Japan under accession number FERM BP-3195), *E. coli* JM109/pNLH122, containing plasmid pNLH122 having the 5' half of a gag gene (deposited at the Fermentation Research Institute, Japan under accession number FERM BP-3196), *E. coli* JM109/pTG581, containing plasmid pTG581 having the entire region of the gag gene (deposited at the Fermentation Research Institute, Japan under accession number FERM BP-3927), *E. coli* JM109/pNS210, containing plasmid pNS210 having the entire region of the env gene (deposited at the Fermentation Research Institute, Japan under accession number FERM BP-3920), *E. coli* JM109/pTE192, containing plasmid pTE192 having a cDNA coding for the Env (512-611) region of the Env protein (deposited at the Fermentation Research Institute, Japan under accession number FERM BP-3925), and *E. coli* JM109/pGE33, containing plasmid pGE33 having a cDNA coding for a Gag-Env fusion protein consisting of Gag(308-406) and Env(512-611) (deposited at the Fermentation Research Institute, Japan under accession number FERM BP-3923). Preparation of cDNA fragments from these clones can be performed according to conventional methods. For example, a desired DNA fragment is cleaved out from the above-mentioned clones by means of restriction enzymes and purified by the technique of phenol extraction, chloroform treatment, ethanol precipitation, or the like. The restriction enzymes to be used for cleaving DNA can be appropriately chosen, based on the restriction maps of the individual clones.

(2) Construction of plasmids for expression of the gag gene, env gene, and gag-env fusion gene, and preparation of transformants having such plasmids inserted therein:

The HIV gene cDNA fragment prepared according to the above procedure is fused to a highly expressing gene on a plasmid or a vector for directly expressing a cloned gene according to conventional methods, e.g., by the use of T4 DNA ligase, to thereby construct an HIV gene expression plasmid. In the present invention, the term "plasmid" is employed as a convenient indication, and in substance, broadly means a replicon which expresses the HIV gene.

Accordingly, for constructing such expression plasmids, conventional and commercially available vectors for expression can be employed. Examples of suitable vectors include the plasmid vector pSN508 series of the enterobacteria family (see U.S. Pat. No. 4,703,005), plasmid vector pJM105 from yeast (see Japanese Patent Application Laid-Open Specification No. 62-286930), plasmid vector pBH103 series from yeast (see Japanese Patent Application Laid-Open Specification No. 63-22098), attenuated varicella virus vector (see Japanese Patent Application Laid-Open Specification No. 53-41202), attenuated Marek's disease virus vector (see European Patent Application Publication No. 334530), plasmid vectors from *Escherichia coli*, such as the pUR290 series, including pUR290, 291, and 292 (see EMBO Journal, 2, 1791–1794, 1983), pSN5182 (see *Journal of Bacteriology*, 157, 909–917, 1984), and the pT7 series (see *Proceedings of the National Academy of Sciences USA* 82, 1074–1078, 1985).

In constructing an expression vector, it is important to insert and ligate the above gene under the control of a strong promoter and to fuse the gene with a gene ensuring expression in large quantity. For example, when the above pUR290 series vector is used, it is preferred that the above gene be fused thereto downstream of the lacZ gene. When pSN5182 is used, the gene is preferably fused downstream of the pstS gene. When pT7-7 of the above pT7 series is used, the gene is preferably cloned into a multicloning site downstream of the T7 promoter.

pT7-7 is especially suitable for the expression of the gag gene, env gene, and gag-env fusion gene of HIV, and the T7 promoter thereof is an extremely strong promoter. Therefore, it is especially preferred to use pT7-7 in the present invention.

In the insertion and ligation of the gene, it is requisite that the plasmid cleaved with a restriction enzyme be pretreated by BAP (bacterial alkaline phosphatase) to remove a phosphate group, thereby preventing self-ligation thereof, and that the reading frame of the gene on the plasmid and that of the inserted gene be arranged to match with each other in order to ensure efficient translation. That is, the expression of the HIV gene in large quantity is guaranteed by inserting the HIV gene into a highly expressing gene in a manner such that the reading frame of the HIV gene matches with that of the highly expressing gene. The above-mentioned matching of reading frames can be attained by conventional methods using enzymes, such as restriction enzymes, nuclease Bal31 and mung been nuclease.

A suitable host cell, into which the above constructed expression vector is to be introduced in order to obtain a transformant, should be selected from sensitive host cells which permit replication and expression of the genes on the expression vector and, especially, from cells which allow the constructed expression vector to be easily introduced thereinto and to be easily detected. For example, when the above-mentioned pSN series vector is used as an expression vector, *Escherichia coli* strain C75 (deposited at the Fermentation Research Institute, Japan under accession number 10191) is preferably employed as the host bacterium, because the transformant obtained by the insertion of the above vector can be screened using its drug resistance as a marker. When pUR290 series and pT7 series vectors are employed, use is made of *Escherichia coli* strain UT481 (see *Journal of Bacteriology*, 163(1), 376–384, 1985), *Escherichia coli* strain BL21 (DE3) (see *Journal of Molecular Biology*, 189(1), 113–130, 1986), *Escherichia coli* strain JM109 (DE3) (see *Journal of Molecular Biology*, 189(1), 113–130, 1986; and *Gene*, 33(1), 103–119, 1985), and *Escherichia coli* strain JM103 (see *Nucleic Acids Research*, 9, 309–321, 1981). These are preferably used because the transformant obtained by the introduction of the vectors can be screened using ampicillin resistance as a marker.

The introduction of an expression vector into such host cells as mentioned above can be carried out by conventional methods, such as the method using potassium chloride (see *Journal of Molecular Biology*, 53, 154–162, 1970). The transformants having, introduced therein, an expression plasmid carrying the gag gene, env gene, or gag-env fusion gene are screened from colonies which are positive for the above-mentioned marker. Subsequently, the expression vector DNA is extracted from the screened transformant colonies, digested with a restriction enzyme and then subjected to agarose gel electrophoresis to determine the size of the inserted DNA fragment. The colony in which the presence of the DNA fragment of the gene has been confirmed is employed as a transformant clone for the expression of the HIV gene.

(3) Production of a LacZ (β-galactosidase)-Env fusion protein in large quantity:

According to the procedure shown in item (2) above, the expression of a LacZ-Env fusion protein in large quantity can be conducted. For example, the large-quantity expression of fusion proteins can be performed by cloning env gene fragments (shown in Table 1), which code for a variety of Env peptides shown in item (5) below, into pUR290, pUR291, or pUR292. With respect to the LacZ-Env fusion protein, it is possible that the β-galactosidase (LacZ) may react with sera from some asymptomatic HIV carriers and non-infected humans, thereby exhibiting false positivity. However, for example, if test sera are pretreated so as to preadsorb anti-LacZ antibodies in the sera with LacZ protein or the LacZ moiety of the fusion protein is masked with anti-LacZ antibodies, according to conventional methods, the above-mentioned false positive reaction can be suppressed, thereby allowing the use of the LacZ-Env fusion protein as an antigen for diagnosis of AIDS.

(4) Confirmation of the expression of the gag gene, env gene, and gag-env fusion gene in transformant clones:

The confirmation of gene expression by transformant clones obtained in item (2) above can be carried out by analyzing a crude extract of transformant clones by a conventional method, such as polyacrylamide gel electrophoresis (PAGE) and Western blotting. The crude extract can be prepared by a method in which after culturing transformants in a conventional medium, the bacterial cells are collected by low-speed centrifugation and then are treated with sodium dodecyl sulfate (SDS) and 2-mercaptoethanol, followed by high-speed centrifugation to thereby collect the supernatant. The supernatant is subjected to SDS-PAGE to thereby fractionate it into protein bands. The fractionated bands are stained with CBB (Coommassie Brilliant Blue) to thereby confirm whether or not large-quantity expression has been attained. When the Western blotting method is employed, the confirmation of the large-quantity expression can be made by the following procedure according to conventional methods using materials selected from a wide variety of commercially available materials: The above-mentioned crude extract is subjected to SDS-PAGE. The resultant fractionated protein bands are transferred onto a nitrocellulose membrane or a polyvinylidene difluoride membrane by the use of a transblotting cell. The membrane is immersed in a gelatin solution or a skim milk solution, thereby blocking the membrane. Thereafter, for example, when the samples on the membrane to be examined are gene expression products of HIV, they are subjected to a primary reaction with serum from asymptomatic HIV carriers. Then, after rinsing the samples, they are further subjected to a secondary reaction with a peroxidase-conjugated anti-human IgG antibody. Then, after rinsing the samples, they are subjected to coloring, using a hydrogen peroxide solution and a coloring agent, to detect bands which specifically react with sera from HIV carriers, thereby confirming the expression of the gag gene, env gene, and gag-env fusion gene of HIV in the above-mentioned clones.

(5) Determination of a partial region of an Env peptide containing epitopes reactive with HIV antibodies:

The determination can be achieved, for example, utilizing the reactivity of the LacZ-Env fusion protein described in item (3) above, by the Western blotting method described in item (4) above. According to this method, it has been found that with respect to the Env protein of the entire amino acid sequence shown in FIGS. 2-(1) to FIG. 2-(3), partial regions which are reactive with HIV antibodies include those having the following amino acid sequences:

Env(14-244), Env(14-437),
Env(14-611), Env(175-363),
Env(224-510), Env(244-611),
Env(244-434), Env(244-437),
Env(244-772), Env(244-826),
Env(437-510), Env(437-611),
Env(437-722), Env(437-826),
Env(512-611), Env(512-699),
Env(610-722), Env(610-826), and
Env(721-826).

Among the above-mentioned amino acid sequences, the following amino acid sequences, which exhibit especially strong reactivity with HIV antibodies, are identified as containing epitopes of the Env protein:

Env(14-244), Env(244-434),
Env(244-510), Env(512-611),
Env(512-699), Env(610-722), and
Env(721-826).

In the present invention, as mentioned above, among the epitope regions of these 7 amino acid sequences, at least a part of the amino acid sequence represented by Env(512-699), which part contains at least one epitope reactive with an HIV antibody, is employed from the viewpoint of attaining excellent antigenicity and productivity of a Gag-Env fusion protein as an HIV antigen of the present invention. The epitope contained in the part of the Env peptide is preferably a contiguous sequence of at least 5 amino acids of the amino acid sequence represented by Env(512-699).

(6) Determination of a Gag peptide which is preferred for the construction of a Gag-Env fusion protein:

In a Gag-Env fusion protein, a Gag peptide is used, instead of LacZ, as a carrier effective for producing an Env peptide in high yield. Therefore, with respect to a Gag peptide, the productivity is more important than the antigenicity. Therefore, after constructing an expression vector for a gag gene according to, for example, the procedure described in item (2) above, the productivity of a Gag peptide is determined by SDS-PAGE in the same manner as in item (4) above.

It has been found that Gag peptides, which can be successfully used for producing a Gag-Env fusion protein in high yield, are represented by the following amino acid sequences:

Gag(1-119), Gag(1-132), Gag(1-154),
Gag(1-210), Gag(1-309), Gag(1-405),
Gag(1-406), Gag(1-437), Gag(1-500),
Gag(121-405), Gag(121-406),
Gag(121-437), Gag(308-405),
Gag(308-406), Gag(308-435),
Gag(308-436), Gag(308-437), and
Gag(308-500).

Of these, Gag(308-437) is one of the amino acid sequences which are most highly accumulated in *E. coli* cells, and hence is useful for assuring the high yield of a Gag-Env fusion protein in the present invention. As mentioned above, in the present invention, the Gag peptide of the Gag-Env fusion protein comprises a contiguous sequence of at least 10 amino acids, preferably at least 30 amino acids, more preferably at least 50 amino acids, still more preferably at least 70 amino acids of the amino acid sequence represented by Gag(308-437). As a Gag peptide of the Gag-Env fusion protein, most preferably employed is a peptide having an amino acid sequence represented by Gag(308-406) or Gag(308-437).

(7) Production of a Gag-Env fusion protein:

A preferred Gag-Env fusion protein is composed of a Gag peptide selected in item (6) above and an Env peptide selected in item (5) above. A plasmid expressing such a fusion protein can be constructed, for example, by inserting a gene coding for an Env peptide described in item (5) above to a plasmid expressing a Gag peptide alone, which Gag peptide is described in item (6) above, or a gag gene-containing plasmid prepared from, e.g., a gag-pol fusion gene, according to the procedure described in items (1) and (2) above. The fusion of a gag gene and an env gene is performed in a fashion such that the reading frame of the inserted env gene matches that of the gag gene on the expression plasmid. This can be achieved by conventional methods employing enzymes, such as restriction enzymes, nuclease Ba131 and mung been nuclease. In this operation, a Gag peptide and an Env peptide may be fused together through a junction consisting of several amino acid residues. It is well known in the art that such a junction is generally incorporated into fusion proteins as a result of the above operation. It does not adversely affect the antigenicity of the Gag-Env fusion protein of the present invention. Accordingly, the expression "Gag-Env fusion protein which consists of a Gag peptide and an Env peptide" and expressions similar thereto should be interpreted to include a Gag-Env fusion protein which consists of a Gag peptide, an Env peptide and a junction, if any, present therebetween. The confirmation of large-quantity expression can be carried out in the same manner as described in item (4) above.

(8) Production of a Gag protein or a Gag-Env fusion protein by culturing a transformant which has been confirmed with respect to the expression of the gag gene or gag-env fusion gene:

For example, the following steps can be taken. For preparing a transformant seed to be cultured for the large-quantity production of a protein, when the transformant is, for example, *E. coli*, it is cultured at 30° to 40° C. for 12 to 35 hours in LB medium until the cell density of *E. coli* reaches $2\times10^9$ to $8\times10^9$ cells/ml. Subsequently, 1 to 10 liters of the seed are inoculated into 1000 liters of fresh LB medium, followed by two-stage culturing consisting of preculturing and postculturing. The purpose of the preculturing is to proliferate seed cells and replicate the expression vector, and the preculturing is carried out at 10° to 40° C. for 1 to 24 hours, preferably 15° to 37° C. for 2 to 12 hours. For example, in the case of *E. coli*, the preculturing is discontinued when the cell density of *E. coli* has reached an $OD_{600nm}$ of 0.1 to 2.0. After the termination of the preculturing, the resultant culture is subjected to postculturing. The postculturing is to be performed under strictly controlled conditions under which the transcription and translation of a gene cloned into an expression vector are insured and, simultaneously, random decomposition and inactivation of gene products produced by translation, by proteolytic enzymes present in host cells, can be avoided. The postculturing is preferably carried out at a temperature lower than that of the preculturing. The postculturing may be performed at 10° to 40° C. for 1 to 40 hours, preferably at 15° to 37° C. for 3 to 35 hours. Further, taking into consideration the properties of the expression vector used, in order to promote and induce the expression, starvation of phosphate in the culture medium, addition of an inducer [such as IPTG (isopropyl β-D-thiogalactopyranoside)] to the culture, and the like, can be conducted at the beginning of the postculturing. By carrying out the above two-stage culturing, the Gag protein or the Gag-Env fusion protein are generally produced in a yield of about 1 to 50 mg per liter of the culture. Among various combinations of Gag peptides and Env peptides as mentioned hereinbefore, the fusion proteins which can be produced in high yield and exhibit especially high antigenicity are Gag-Env fusion proteins respectively having amino acid sequences represented by: Gag(308-406)-Env(512-611), Gag(308-437)-Env(512-611), and Gag(308-406)-Env(512-699).

(9) Purification of the Gag protein and Gag-Env fusion protein which have been produced in high yield:

This can be achieved by employing conventional methods in combination. For example, purification of proteins can be carried out by an appropriate combination of the following methods: (a) collection of transformed cells by the use of a precipitant, centrifugation, filtration, etc.; (b) preparation of a crude extract by disrupting transformed cells by the use of ultrasonic treatment, pressure/vacuum treatment, a homogenizer, etc.; (c) purification by adsorption and desorption with silicic acid or an activated carbon, salting out, precipitation from an organic solvent, etc., as well as high degree of purification by fractionation employing ultracentrifugation, column chromatography, electrophoresis, etc.; and (d) purification by adsorption and desorption with silicic acid or activated carbon and fractionation by density gradient centrifugation (see Japanese Patent Application Laid-Open Specification No. 63-297).

Accordingly, in still another aspect of the present invention, there is provided a method for producing a substantially pure HIV antigen comprising a Gag-Env fusion protein, wherein the Gag-Env fusion protein consists of a Gag peptide fused at its C-terminus to an Env peptide, which comprises:

(a) ligating a first deoxyribonucleic acid sequence to a replicable expression vector to obtain a first recombinant DNA molecule capable of replication in a host cell and comprising said expression vector and said first deoxyribonucleic acid sequence inserted therein, the first deoxyribonucleic acid sequence coding for a Gag peptide comprising a contiguous sequence of at least ten amino acids of the amino acid sequence represented by Gag (308-437), wherein each of the numbers indicated in the parentheses is the positional amino acid number in the entire amino acid sequence of the Gag protein shown in FIGS. 1-(1) through 1-(2);

(b) ligating a second deoxyribonucleic acid sequence to the first recombinant DNA molecule downstream of the first deoxyribonucleic acid sequence, so that the second sequence is fused to the first sequence, the second deoxyribonucleic acid sequence coding for an Env peptide comprising at least a part of the amino acid sequence represented by Env (512-699), the part containing at least one epitope which is reactive with an HIV antibody, wherein each of the numbers indicated in the parentheses is the positional amino acid number in the entire amino acid sequence of the Env protein shown in FIGS. 2-(1) through 2-(3), thereby obtaining a second recombinant DNA molecule capable of replication in a host cell and comprising the expression vector, the first deoxyribonucleic acid sequence, and the second deoxyribonucleic acid sequence fused downstream of the first sequence;

(c) transforming prokaryotic or eukaryotic cells with the second recombinant DNA molecule to produce transformants;

(d) selecting the transformants from untransformed prokaryotic or eukaryotic cells;

(e) culturing the transformants to produce an HIV antigen comprising a Gag-Env fusion protein, wherein the Gag-Env fusion protein consists of the Gag peptide fused at its C-terminus to the Env peptide; and (f) isolating the HIV antigen comprising the Gag-Env fusion protein from the cultured transformants.

It is preferred that the second deoxyribonucleic acid code for a contiguous sequence of at least five amino acids of the amino acid sequence represented by Env (512-699).

The above-mentioned first deoxyribonucleic acid codes for a Gag peptide comprising a contiguous sequence of at least ten amino acids of the amino acid sequence represented by Gag (308-437). The first deoxyribonucleic acid codes for a Gag peptide comprising a contiguous sequence of preferably at least 30 amino acids, more preferably at least 50 amino acids, still more preferably at least 70 amino acids of the amino acid sequence represented by Gag (308-437). Most preferably, the first deoxyribonucleic acid codes for a Gag peptide comprising the amino acid sequence represented by Gag (308-406) or Gag (308-437).

From the viewpoint of attaining improved antigenicity and productivity of the Gag-Env fusion protein, it is required that the second deoxyribonucleic acid sequence code for an Env peptide comprising at least a part of the amino acid sequence represented by Env (512-699), which part contains at least one epitope which is reactive to an HIV antibody. The second deoxyribonucleic acid codes for a contiguous sequence of preferably at least five amino acids, more preferably at least ten amino acids, most preferably at least 15 amino acids of the amino acid sequence represented by Env (512-699).

It is preferred that the expression vector be derived from the pT7 series or the pUR290 series vectors. Most preferably, the expression vector is pT7-7.

The expression vector obtained in the method of the present invention may be provided in a form contained in a sealed small vessel, such as an ampule or a vial, or in a form incorporated into a host cell.

In a further aspect of the present invention, there is provided a recombinant DNA molecule capable of replication in a host cell, comprising a replicable expression vector having inserted therein a first deoxyribonucleic acid sequence, and a second deoxyribonucleic acid sequence fused downstream of the first sequence, the first deoxyribonucleic acid sequence coding for a Gag peptide comprising a contiguous sequence of at least ten amino acids of the amino acid sequence represented by Gag (308-437), wherein each of the numbers indicated in the parentheses is the positional amino acid number in the entire amino acid sequence of the Gag protein shown in FIGS. 1-(1) through 1-(2), and the second deoxyribonucleic acid sequence coding for an Env peptide comprising at least a part of the amino acid sequence represented by Env (512-699), the part containing at least one epitope which is reactive to an HIV antibody, wherein each of the numbers indicated in the parentheses is the positional amino acid number in the entire amino acid sequence of the Env protein of HIV shown in FIGS. 2-(1) through 2-(3).

It is preferred that the second deoxyribonucleic acid sequence code for a contiguous sequence of at least five amino acids of the amino acid sequence represented by Env (512-699).

As more preferred forms of the first deoxyribonucleic acid sequence and second deoxyribonucleic acid sequence of the recombinant DNA molecule of the present invention, those which are described above in connection with the method for producing the Gag-Env fusion protein of the HIV antigen of the present invention can be used.

It is preferred that the expression vector be selected from those which are derived from the pT7 series or the pUR290 series vectors. Most preferably, the expression vector is pT7-7.

The Gag protein and Gag-Env fusion protein produced in large quantity by using the recombinant DNA molecule of the present invention may be charged and sealed in a small vessel, such as an ampule or a vial, in the form of a liquid or dried powder, or in a form adsorbed on a filter or membrane. When the antigen of the present invention is in a liquid form, a predetermined volume can be taken out and used. When the antigen is in a dried form, the antigen is dissolved in distilled water for reconstitution thereof so that the volume becomes the original volume before being subjected to drying and then, a predetermined volume can be taken and used. When the antigen is in an adsorbed form on a filter or membrane, the antigen is hydrated with an appropriate solution, and used.

In still a further aspect of the present invention, there is provided a reagent for diagnosis of acquired immune deficiency syndrome by an immunological reaction, comprising an immunological reaction effective amount of the HIV antigen of the present invention comprising a Gag-Env fusion protein and/or a Gag protein.

In still a further aspect of the present invention, there is provided a vaccine for acquired immune deficiency syndrome, comprising an effective immunogenic amount of the HIV antigen of the present invention comprising a Gag-Env fusion protein and/or a Gag protein and at least one pharmaceutically acceptable adjuvant, diluent, or excipient.

The dose of the vaccine for adults at one administration may generally be about 0.001 to 1000 μg.

The present invention will now be described in more detail with reference to the following Examples, which should not be construed to limit the scope of the present invention.

PREFERRED EMBODIMENT OF THE INVENTION

Example 1

Step 1 (Construction of plasmids capable of expressing LacZ-Env fusion proteins)

HIV-1 provirus DNA clone pNL4-3 (see *Journal of Virology*, 59, 284–291, 1986; GenBank data file HIVNL43; which clone pNL4-3 is available from the National Institutes of Health, U.S.A.) is digested with EcoRI and XhoI and then subjected to agarose gel electrophoresis to thereby obtain a DNA fragment of 3.1 kb [nucleotide number 5743-8887 according to GenBank data file HIVNL43]. The obtained DNA fragment is cloned into plasmid pHSG398 which has been digested with EcoRI and SalI and treated with BAP, to thereby obtain plasmid pNS210. The obtained plasmid pNS210 is digested with KpnI and then subjected to agarose gel electrophoresis to thereby obtain a DNA fragment of 2.55 kb. The collected DNA fragment is digested with HaeIII and then subjected to agarose gel electrophoresis to thereby obtain a HaeIII DNA fragment of about 570 b [nucleotide number 7834-8400 according to GenBank data file HIVNL43]. The obtained DNA fragment is cloned into plasmid pUC9 which has been digested with HincII and treated with BAP, to thereby obtain plasmid pEH22. The obtained plasmid pEH22 is digested with BamHI and PstI to obtain a DNA fragment of about 580 b, and the obtained DNA fragment is cloned into plasmid pUR292 (see *EMBO Journal*, 2, 1791∝1794, 1983) which has been cleaved with BamHI and PstI, to thereby obtain plasmid pAS182 (see Table 1). The obtained plasmid pAS182 is digested with HindIII and then self ligated to thereby obtain plasmid pAS192 (see Table 1). The obtained plasmids pAS182 and pAS192 express LacZ-Env (512-699) and LacZ-Env (512-611) fusion proteins, respectively. In addition to the above plasmids, 15 other types of plasmids which express various types of LacZ-Env fusion proteins are constructed (see Table 1).

Step 2 (Large-quantity production of LacZ-Env fusion proteins)

17 types of expression vectors shown in Table 1 including plasmids pAS182 and pAS192 are individually introduced into *E. coli* strain JM 103 (see *Nucleic Acids Research*, 9, 309–321, 1981). The resultant *E. coli* transformants are individually inoculated into 2 ml of LB medium containing 20 μg/ml of ampicillin and incubated at 37° C. overnight with shaking, to obtain cultures. Then, 0.05 to 0.1 ml of each of the cultures is inoculated into 5 ml of LB medium containing 20 μg/ml of ampicillin and then incubated at 37° C. with shaking. When the cell density reaches an $OD_{600nm}$ of 0.5, IPTG is added to the culture to a final concentration of 1 mM to thereby induce expression of fusion proteins. The culture is incubated at 37° C. for 5 hours with shaking and then the *E. coli* cells are harvested from 1.5 ml of the culture by centrifugation. The harvested cells are suspended in 120 μl of 20 mM Tris-HCl (pH 7.5) to thereby obtain a suspension. To the obtained suspension is added 60 μl of SDS-PAGE sample buffer, and mixed well. The mixture is heated at 100° C. for 3 minutes and centrifuged at 12,000 rpm for 5 minutes, to thereby obtain a supernatant. 7.5 μl of the obtained supernatant is applied to an SDS-PAGE gel to thereby attain fractionation. The gel is stained with CBB to confirm production of fusion proteins. Thus, large-quantity production of 17 types of LacZ-Env fusion proteins is confirmed.

Step 3 (Identification of epitope regions which are recognized by Env antibodies in sera of HIV carriers)

The total proteins of *E. coli* strain JM103 which has been used in the large-quantity production of 17 types of LacZ-Env fusion proteins (see Table 1) and LacZ protein are fractionated by SDS-PAGE in substantially the same manner as in Step 2, and electroblotted to a polyvinylidene difluoride membrane. The blots are blocked with skim milk (available from Difco Laboratories, U.S.A.), and individually reacted with each of sera A, B, and C, separately, which have been taken from three HIV carriers (asymptomatic HIV carriers) and diluted to 100-fold with a buffer containing 20 mM Tris-HCl (pH 7.5), 150 mM NaCl, and 0.05% Tween 20. Before the use of the sera, it has been confirmed that none of the sera reacts with LacZ. As a secondary antibody, use is made of a peroxidase-conjugated goat anti-human IgG (Bio-Rad Laboratories, U.S.A.). By analyzing the results (see Table 2) of the Western blotting, two, three, and five epitope regions recognized by Env antibodies contained in the sera A, B, and C are identified, respectively (see Table 3). The fusion proteins that react with all of sera A, B, and C are LacZ-Env fusion proteins containing an amino acid sequence of Env (512-611) and/or an amino acid sequence of Env (721-826).

Step 4 (Evaluation of LacZ-Env (512-611) and LacZ-Env (721-826) fusion proteins as antigens for diagnosis)

For confirming the usefulness of LacZ-Env (512-611) and LacZ-Env (721-826) fusion proteins as antigens for diagnosis, Western blotting is conducted in substantially the same manner as in Step 3 using sera from 41 HIV carriers (in particular, 36 asymptomatic HIV carriers, 1 ARC and 4 AIDS patients). The results of Western blotting are shown in Table 4, together with those of 3 asymptomatic HIV carriers of Step 3. LacZ-Env (512-611) reacts with all of the sera from 44 HIV carriers (100%). On the other hand, LacZ-Env (721-826) reacts with only 35 out of 44 HIV carriers (79%). Therefore, Env (512-611) is considered to be useful as an antigen for diagnosis. The Env (721-826) region cannot be independently used for diagnosis, but it would be useful in combination with other antigens, for example, the Env (512-611) region. However, sera from 2 out of 39 asymptommatic HIV carriers weakly react with LacZ (β-galactosidase) and, therefore, it would be undesirable to use the LacZ-Env fusion protein as it is for diagnostic purposes. However, the LacZ-Env fusion protein can be used for diagnostic purposes if test sera are pretreated so as to preadsorb anti-LacZ antibodies in the sera with LacZ protein according to the customary method, as mentioned hereinbefore.

Step 5 (Construction of plasmids capable of expressing Env proteins under the control of the T7 promoter)

Synthetic oligonucleotides 5' TATGGCTAAG 3' SEQ. ID NO:3 and 5' AATTCTTAGCCA 3' are annealed, and inserted into plasmid pT7-7, a plasmid of the pT7 series (see *Proceedings of the National Academy of Sciences USA*, 82, 1074–1078, 1985), having been digested with NdeI and EcoRI, to thereby obtain plasmid pT7-7-1. The plasmid pT7-7-1 is the plasmid having a one nucleotide insertion of an adenine residue (A) between the NdeI site and the EcoRI site being multicloning sites of pT7-7. The plasmid pT7-7-1 is digested with BamHI and PstI, and the fragment of about 580 b obtained by digesting plasmid pEH22 (see Step 1) with BamHI and PstI is cloned thereinto to thereby obtain plasmid pTE182 (see Table 5). Subsequently, the thus obtained plasmid pTE182 is digested with HindIII, and then self ligated to thereby obtain plasmid pTE192 (see Table 5). Plasmid pNS210 (see Step 1) is digested with NdeI, and further partially digested with BglII to thereby obtain an NdeI-BglII fragment (nucleotide number 6399-7611 according to GenBank data file HVNL43). The thus obtained NdeI-BglII fragment is cloned into plasmid pUR292 (see Step 1) having been digested with NdeI and BamHI to thereby obtain plasmid pNB21. The obtained plasmid pNB21 is digested with BglII and ClaI to thereby obtain a fragment of about 0.6 kb. The obtained fragment is cloned into plasmid pT7-7 having been digested with BamHI and ClaI to thereby obtain plasmid pTE311 (see Table 5). The obtained plasmids pTE182, pTE192, and pTE311 express Env (512-699), Env (512-611), and Env (244-437), respectively. Plasmids capable of expressing an Env protein under the control of the T7 promoter are shown in Table 5. *E. coli* strain BL21 (DE3) is used as a host for expression. The culturing of *E. coli* cells and the analysis of proteins are conducted in substantially the same manner as described in Steps 2 and 3. The proportion of the Env proteins expressed by plasmids pTE182, pTE192, and pTE311 to the total cell proteins is as small as only about 1 to 2%. This shows that even if a plasmid is chosen, it is difficult to express an Env protein alone in a practically acceptable yield.

Step 6 (Construction of plasmids capable of expressing Gag proteins under the control of the T7 promoter)

Plasmid pTG591 (see Japanese Patent Application Laid-Open Specification No. 4-117289) is digested with NdeI and BclI to obtain a fragment of about 1.6 kb. This fragment is cloned into plasmids pT7-7 and pTE-3a (see *Methods in Enzymology*, 185, 60–89, 1990) each having been digested with NdeI and BamHI, to thereby obtain plasmids pTG581 and pEG581 (see Table 6), respectively. These plasmids express the gag gene (p55).

Plasmids pTG210, pTG110, and pTG591 (see Japanese Patent Application Laid-Open Specification No. 4-117289) are individually digested with ApaI and ClaI, treated with T4DNA polymerase, and self ligated, to thereby obtain plasmids pTG210-2, pTG110-2, and pTG561 (see Table 6), respectively. These plasmids are, respectively, capable of expressing Gag (308-405), Gag (121-405), and Gag (1-405). The plasmids which express Gag proteins under the control of the T7 promoter are shown in Table 6. *E. coli* strain BL21 (DE3) is used as a host for the expression. Culturing of *E. coli* cells and analysis of the obtained proteins are conducted in substantially the same manner as in Steps 2 and 3.

Step 7 (Construction of plasmids capable of expressing Gag-Env fusion proteins under the control of the T7 promoter)

Plasmid pAS192 (see Step 1) is digested with BamHI, treated with T4DNA polymerase, and digested with ClaI, followed by agarose gel electrophoresis. From the agarose gel, a fragment of about 310 b is recovered. This fragment is cloned into plasmid pTG210 (see Japanese Patent Application Laid-Open Specification No. 4-117289) having been digested with ApaI, treated with T4DNA polymerase and digested with ClaI to thereby obtain plasmid pGE33 (see Table 7). The obtained plasmid pGE33 is digested with HindIII and then subjected to agarose gel electrophoresis. From the agarose gel a fragment of about 600 b is recovered. This fragment is cloned into plasmids pTG110 and pTG591 (see Japanese Patent Application Laid-Open Specification No. 4-117289) each having been digested with HindIII and treated with BAP, to thereby obtain plasmids pGE1133 and pGE5633 (see Table 7), respectively. The obtained plasmids pGE33, pGE1133, and pGE5633 express fusion proteins Gag(308-406)-Env(512-611), Gag(121-406)-Env(512-611), and Gag(1-406)-Env(512-611), respectively.

The nucleotide sequence between the BamHI site and the HindIII site of the multicloning sites of plasmid pT7-7-1 (see Step 5) is replaced with that of plasmid pUR292 (see Step 1) to thereby obtain plasmid pT7-29-1. The obtained pT7-29-1 is digested with BamHI, treated with T4DNA polymerase, and self ligated to thereby obtain plasmid pT7-29-14. The above-mentioned plasmid pGE33 is digested with HindIII to thereby obtain a fragment of about 0.6 kb, and this fragment is cloned into plasmid pT7-29-14 having been digested with HindIII and treated with BAP, to thereby obtain plasmid pGE2133.

Plasmid pAS182 (see Step 1) is digested with BamHI and ClaI to obtain a fragment of about 590 b. This fragment is cloned into plasmids pGE2133 and pGE1133 each having been digested with BamHI and ClaI, to thereby obtain plasmids pGE218 and pGE118, respectively (see Table 7). Plasmids pGE218 and pGE118 express fusion proteins Gag(308-406)-Env(512-699) and Gag(121-406)-Env(512-699), respectively.

Plasmid pT7-7 (see Step 5) is digested with BglII, treated with T4DNA polymerase, and self ligated to thereby obtain plasmid pT7-7 (BglIIx). Plasmid pTG210 (see Japanese Patent Application Laid-Open Specification No. 4-117289) is digested with NdeI and ClaI to obtain a fragment of about 1 kb. This fragment is cloned into plasmid pT7-7 (BglIIx) having been digested with NdeI and ClaI to thereby obtain plasmid pTG210X.

Plasmid pAS192 (see Step 1) is digested with BamHI and ClaI to obtain a fragment of about 310 b. This fragment is cloned into plasmid pTG210X having been digested with BglII and ClaI, to thereby obtain plasmid pGE31 (see Table 7). Plasmid pGE31 expresses fusion protein Gag(308-437)-Env(512-611).

Plasmids which express Gag-Env fusion proteins under the control of the T7 promoter are shown in Table 7. *E. coli* strain BL21 (DE3) is used as a host for expression. Culturing of *E. coli* cells to attain large-quantity production of a fusion protein and analysis of the protein are conducted in substantially the same manner as in Steps 2 and 3.

The total cell proteins of the *E. coli* cells which have produced fusion proteins shown in Table 7 are fractionated by SDS-PAGE, and the gels are stained with CBB. By scanning the gel with a densitometer, the proportions of the produced fusion proteins to the total cell proteins are measured. The greatest proportion is exhibited with respect to the fusion proteins expressed by plasmids pGE33, pGE218, and pGE31, which is about 20%.

Step 8 (Confirmation of the reactivity of Gag-Env fusion protein with HIV antibodies)

Plasmids pGE33, pGE31, and pGE218 constructed in Step 7 express large quantities of Gag-Env fusion proteins in *E. coli* strain BL21 (DE3). Of these fusion proteins, the protein produced in an especially large quantity is Gag(308-406)-Env(512-611) fusion protein expressed by pGE33. In order to confirm the usefulness of this fusion protein as an antigen for diagnosis, the reaction between the fusion protein and each of sera taken from 41 HIV carriers (36 asymptomatic HIV carriers, 1 ARC, and 4 AIDS patients) is investigated by conventional Western blotting in substantially the same manner as described in Steps 2 and 3 (see Table 8). As a result, it is found that Env antibodies can be detected in all of the 41 carriers, thus assuring the usefulness of the fusion protein as an antigen for diagnosis.

Step 9 (Purification of the Gag(308-406)-Env(512-611) fusion protein)

250 ml of a culture of *E. Coli* strain BL21 (DE3) which has produced the Gag(308-406)-Env(512-611) fusion protein in large quantity, is subjected to centrifugation at 5,000 rpm for 10 minutes to thereby harvest the *E. coli* cells. The harvested cells are suspended in 10 ml of a buffer containing 50 mM Tris-HCl (pH7.5) and 10 mM 2-mercaptoethanol, and the resultant suspension is subjected to ultrasonication to thereby disrupt the cells. When the resultant lysate is centrifuged at 19,000 rpm for 30 minutes, the Gag-Env fusion protein is contained in the precipitate. The supernatant is discarded, and the precipitate is suspended in 10 ml of a buffer containing 50 mM Tris-HCl (pH7.5) and 10 mM 2-mercaptoethanol. To the obtained suspension is added 5 ml of SDS-PAGE sample buffer (for sodium dodecyl sulfate-polyacrylamide gel electrophoresis), mixed well, and heated at 100° C. for 5 minutes. The heated mixture is centrifuged at 12,000 rpm for 5 minutes, and 2 ml (per batch) of the resultant supernatant is applied to an SDS-PAGE gel of a Model 491 PrepCell (available from Bio-Rad Laboratories, U.S.A.) to carry out electrophoresis at 40 mA. Chromatography is conducted at a flow rate of 1 ml/min and in a fraction size of 2.5 ml/frac. to thereby collect a peak fraction containing the Gag-Env fusion protein.

The peak fraction is concentrated about 20-fold, and the resultant concentrate is subjected to SDS-PAGE, followed by staining with CBB.

As a result, it is found that the fusion protein is highly purified, with no other protein bands observed.

About 5 mg of purified Gag(308-406)-Env(512-611) fusion protein is obtained from one liter of *E. coli* culture.

Step 10 (Usefulness of the purified Gag-Env fusion protein as an antigen for diagnosis)

The preparation of purified Gag(308-406)-Env(512-611) fusion protein obtained in Step 9 is diluted, and the dilution is dotted onto a polyvinylidene difluoride membrane to obtain dots of the fusion protein in amounts of 10, 20, 40, 80, 160, and 320 ng. The dots are individually blocked with skim milk, and reacted with sera from each of 55 HIV carriers (in particular, 50 asymptomatic HIV carriers, 1 ARC and 4 AIDS patients) and from 84 non-infected individuals (healthy individuals), the sera having been diluted 100-fold with a buffer containing 20 mM Tris-HCl (pH 7.5), 150 mM NaCl and 0.05% Tween 20. Peroxidase-conjugated goat anti-human IgG (available from Bio-Rad Laboratories, U.S.A.) is used as a secondary antibody, and the color reaction is performed by the customary method. Results of the above dot blotting are shown in Table 9.

As little as 20 ng of the fusion protein specifically reacts with all the sera from 55 HIV carriers, and even 5 ng of the fusion protein specifically reacts with all the sera from the HIV carriers except 2 asymptomatic HIV carriers. Neither specific reaction nor non-specific reaction is observed between as much as 320 ng of the fusion protein and the sera from 84 healthy individuals. From these results, it is judged that the purified fusion protein exhibits extremely high specificity and a broad spectrum of seroreactivity, thereby ensuring the usefulness of the protein as an antigen for diagnosis.

Example 2

Step 1 (Production of highly purified Gag protein p55)

A culture of *E. coli* transformant BL21(DE3)/pTG581 having produced a large quantity of Gag protein p55 is centrifuged at 5,000 rpm for 10 minutes to thereby harvest the cells. The harvested cells are suspended in a phosphate buffer containing 20 mM sodium phosphate (pH 6.9) and 10 mM 2-mercaptoethanol, the volume of which is 1/50 that of the above-mentioned culture, and the resultant suspension is subjected to ultrasonication to thereby disrupt the cells. The resultant lysate is centrifuged at 19,000 rpm for 60 minutes to obtain a supernatant containing p55. The supernatant is treated with 20% saturation of ammonium sulfate to thereby obtain a precipitate. The obtained precipitate is dissolved in a phosphate buffer as defined above but containing 8M urea. The resultant solution is passed through a column of S-Sepharose (manufactured and sold by Pharmacia Fine Chemicals AB, Sweden) equilibrated with the same phosphate buffer as mentioned above. Elution is carried out with the buffer having, added thereto, sodium chloride, having a 0 to 1M concentration gradient, thus obtaining p55 fractions. The obtained p55 fractions are pooled. The pooled fractions are dialyzed against a phosphate buffer as defined above but containing 300 mM sodium chloride, followed by centrifugation at 19,000 rpm for 20 minutes. The resultant supernatant is passed through a column of Heparin-Sepharose CL-6B (manufactured and sold by Pharmacia Fine Chemicals AB, Sweden) equilibrated with the above defined phosphate buffer. Elution is performed with the buffer having, added thereto, sodium chloride, having a 0 to 1M concentration gradient, to thereby obtain p55 fractions. The obtained p55 fractions are pooled and then concentrated. To the resultant concentrate is added a sample buffer for SDS-PAGE, and mixed well. The mixture is applied to an SDS-PAGE gel in a Prep Cell. Chromatography is performed under the same conditions as described in Step 9 of Example 1. The resultant p55 fraction is concentrated to about a 20-fold concentration, and the resultant concentrate is subjected to SDS-PAGE, followed by staining with CBB. It is found that p55 is highly purified, with no other protein bands observed. Step 2 (Reactivity of respective Gag proteins p17, p24, and p15 and the entire Gag protein, p55, with sera from HIV carriers, the Gag proteins having been produced in large quantities by *E. coli* and highly purified)

Highly purified HIV-1 Gag proteins p17, p24, p15 (see WO91/18990), and p55 (see Step 1 of Example 2) are individually dotted onto a polyvinylidene difluoride membrane in substantially the same manner as described in Step 10 of Example 1, and reacted with sera from 40 HIV carriers, separately, (in particular, 35 asymptomatic HIV carriers, 1 ARC and 4 AIDS patients) and from 10 non-infected individuals (healthy individuals). A serum reaction and-a coloring reaction are carried out in substantially the same manner as described in Step 10 of Example 1. Results of such reactions are shown in Table 10. Gag proteins p17, p24, and p15 detect specific antibodies in 92.5% (37/40), 87.5% (35/40), and 85% (34/40) of the carriers, respectively. Gag protein p55 specifically reacts with all of the sera from 40 HIV carriers, and the reactions are stronger than those of the p17, p24, and p15. It is especially noted that p55 reacts with the serum from one asymptomatic HIV carrier, which reacts with none of the Gag proteins p17, p24, and p15. The Gag protein which exhibits the weakest reactivity is p15.

With respect to Gag proteins p17, p24, and p55, the reactivity with sera from ARC and AIDS patients is weaker than that with sera from asymptomatic HIV carriers. This phenomenon is not observed with p15. In all of the 10 healthy individuals, no reaction takes place.

From the above results, it is seen that the Gag protein p55 is most excellent as a Gag antigen for screening HIV infection.

TABLE 1

Plasmids for expression of LacZ-Env fusion proteins

| Plasmid | 5' cloning site* | Nt. no. of 5' cloning site* | Nt. no. of 3' cloning site* | 3' cloning site* | Product** |
|---|---|---|---|---|---|
| pAS160 | KpnI | 6343 | 7031 | BglII | LacZ-Env (14-244) |
| pAS210 | KpnI | 6343 | 7611 | BglII | LacZ-Env (14-437) |
| pAS200 | KpnI | 6343 | 8131 | HindIII | LacZ-Env (14-611) |
| pAS172 | StuI | 6822 | 7391 | ScaI | LacZ-Env (175-363) |
| pAS220 | HaeIII | 6969 | 7834 | HaeIII | LacZ-Env (224-510) |
| pAS311 | BglII | 7031 | 7611 | BglII | LacZ-Env (244-437) |
| pAS331 | BglII | 7031 | 8131 | HindIII | LacZ-Env (244-611) |
| pAS111 | BglII | 7031 | 8465 | BamHI | LacZ-Env (244-722) |
| pAS131 | BglII | 7031 | 8887 | XhoI | LacZ-Env (244-826) |
| pAS342 | BglII | 7611 | 8131 | HindIII | LacZ-Env (437-611) |
| pAS122 | BglII | 7611 | 8465 | BamHI | LacZ-Env (437-722) |
| pAS142 | BglII | 7611 | 8887 | XhoI | LacZ-Env (437-826) |
| pAS192 | HaeIII | 7834 | 8131 | HindIII | LacZ-Env (512-611) |
| pAS182 | HaeIII | 7834 | 8400 | HaeIII | LacZ-Env (512-699) |
| pAS351 | HindIII | 8131 | 8465 | BamHI | LacZ-Env (610-722) |
| pAS151 | HindIII | 8131 | 8887 | XhoI | LacZ-Env (610-826) |
| pAS451 | BamHI | 8465 | 8887 | XhoI | LacZ-Env (721-826) |

*Nucleotide sequence and nucleotide number are according to GenBank data file HIVNL43.
**Numbers in parentheses show amino acid numbers counted from the N-terminus of the Env protein (gp160)

TABLE 2

Reactivity shown by Western blotting of LacZ-Env fusion proteins with sera of three asymptomatic HIV-1 carriers

| Plasmid | Product | Serum A | Serum B | Serum C |
|---|---|---|---|---|
| pUR290 | LacZ | – | – | – |
| pAS160 | LacZ-Env (14-244) | – | – | + |
| pAS210 | LacZ-Env (14-437) | – | – | + |
| pAS200 | LacZ-Env (14-611) | + | + | + |
| pAS172 | LacZ-Env (175-363) | – | – | + |
| pAS220 | LacZ-Env (224-510) | – | + | + |
| pAS311 | LacZ-Env (244-437) | – | – | + |
| pAS331 | LacZ-Env (244-611) | + | + | + |
| pAS111 | LacZ-Env (244-722) | + | + | + |
| pAS131 | LacZ-Env (244-826) | + | + | + |
| pAS342 | LacZ-Env (437-611) | + | + | + |
| pAS122 | LacZ-Env (437-722) | + | + | + |
| pAS142 | LacZ-Env (437-826) | + | + | + |
| pAS192 | LacZ-Env (512-611) | + | + | + |
| pAS182 | LacZ-Env (512-699) | + | + | + |
| pAS351 | LacZ-Env (610-722) | – | – | + |
| pAS351 | LacZ-Env (610-826) | + | + | + |
| pAS451 | LacZ-Env (721-826) | + | + | + |

TABLE 3

Identified epitope regions on the Env protein

| | Serum A | Serum B | Serum C |
|---|---|---|---|
| Identified epitope regions | | | Env (14-244) |
| | | Env (224-510) | |
| | | | Env (244-437) |
| | Env (512-611) | Env (512-611) | Env (512-611) |
| | | | Env (610-722) |
| | Env (721-826) | Env (721-826) | Env (721-826) |

TABLE 4

Detection of Env antibodies in sera of HIV-1 carriers

| Antigen | Sera | + | ± | – | Total |
|---|---|---|---|---|---|
| LacZ-Env (512-611) | AC | 39 | – | – | 39 |
| | ARC | 1 | – | – | 1 |
| | AIDS | 4 | – | – | 4 |
| LacZ-Env (721-826) | AC | 34 | 3 | 2 | 39 |
| | ARC | – | 1 | – | 1 |
| | AIDS | 1 | 3 | – | 4 |

TABLE 5

Plasmids for expression of Env proteins of HIV-1

| Plasmid | 5' cloning site* | Nt. no. of 5' cloning site* | Nt. no. of 3' cloning site* | 3' cloning site* | Product** |
|---|---|---|---|---|---|
| pTE160 | KpnI | 6343 | 7031 | BglII | Env (14-244) |
| pTE210 | KpnI | 6343 | 7611 | BglII | Env (14-437) |
| pTE200 | KpnI | 6343 | 8131 | HindIII | Env (14-611) |
| pTE172 | StuI | 6822 | 7391 | ScaI | Env (175-363) |
| pTE17-2 | StuI | 6822 | 7391 | ScaI | Env (175-363) |
| pTE220 | HaeIII | 6969 | 7834 | HaeIII | Env (224-510) |
| pTE311 | BglII | 7031 | 7611 | BglII | Env (244-437) |
| pTE342 | BglII | 7611 | 8131 | HindIII | Env (437-611) |
| pTS23 | BglII | 7611 | 8887 | XhoI | Env (437-826) |
| pTE192 | HaeIII | 7834 | 8132 | HindIII | Env (512-611) |
| pTE18-192 | HaeIII | 7834 | 8131 | HindIII | Env (512-611) |
| pTE182 | HaeIII | 7834 | 8400 | HaeIII | Env (512-699) |
| pTE18-182 | HaeIII | 7834 | 8400 | HaeIII | Env (512-699) |
| pTS45 | BamHI | 8465 | 8887 | XhoI | Env (721-826) |

*Nucleotide sequence and nucleotide number are according to GenBank data file HIVNL43.
**Numbers in parentheses show amino acid numbers counted from the N-terminus of the Env protein (gp160).

Even if an appropriate plasmid is chosen, the expression of the ENV protein alone in a practically acceptable yield is found to be difficult.

TABLE 6

Plasmids for expression of Gag proteins of HIV-1

| Plasmid | 5' cloning site* | Nt. no. of 5' cloning site* | Nt. no. of 3' cloning site* | 3' cloning site* | Product** |
|---|---|---|---|---|---|
| pTG581 | NdeI** | 787 | 2429 | BclI | Gag (1-500) |
| pEG581 | NdeI** | 787 | 2429 | BclI | Gag (1-500) |
| pTG571 | NdeI** | 787 | 2096 | BglII | Gag (1-437) |
| pEG571 | NdeI** | 787 | 2096 | BglII | Gag (1-437) |
| pTG561 | NdeI** | 787 | 2006 | ApaI | Gag (1-405) |
| pTG551 | NdeI** | 787 | 1712 | HindIII | Gag (1-309) |
| pTG541 | NdeI** | 787 | 1415 | PstI | Gag (1-210) |
| pTG531 | NdeI** | 787 | 1247 | NsiI | Gag (1-154) |
| pTG207 | NdeI** | 787 | 1415 | PstI | Gag (1-132)**** |
| pTG521 | NdeI** | 787 | 1145 | PVuII | Gag (1-119) |
| pTG121 | PvuII | 1145 | 2096 | BglII | Gag (121-437) |
| pTG110-2 | PvuII | 1145 | 2006 | ApaI | Gag (121-405) |
| pTG212 | HindIII | 1712 | 2429 | BclI | Gag (308-500) |
| pTG221 | HindIII | 1712 | 2096 | BglII | Gag (308K-437) |
| pTG210-2 | HindIII | 1712 | 2006 | ApaI | Gag (308-405) |

*Nucleotide sequence and nucleotide number are according to GenBank data file HIVNL43.
**NdeI site is introduced by in vitro mutagenesis at the initiation codon of the gag gene.
***Numbers in parentheses show amino acid numbers counted from the N-terminus of the Gag protein (p55).
****Termination codon is introduced at the first codon of p24, leading to the expression of p17.

TABLE 7

Plasmids for expression of Gag-Env fusion proteins

| Plasmid | Product: Gag protein region (a.a.) | Product: Env protein region (a.a.) |
|---|---|---|
| pGE216 | 308-406 | 14-244 |
| pGE116 | 121-406 | 14-244 |
| pGE221 | 308-406 | 14-437 |
| pGE217 | 308-406 | 175-363 |
| pGE117 | 121-406 | 175-363 |
| pGE231 | 308-406 | 244-437 |
| pGE131 | 121-406 | 244-437 |

TABLE 7-continued

Plasmids for expression of Gag-Env fusion proteins

| Plasmid | Product: Gag protein region (a.a.) | Product: Env protein region (a.a.) |
|---|---|---|
| pGE223 | 308-406 | 437-510 |
| pGE123 | 121-406 | 437-510 |
| pGE523 | 1-406 | 437-510 |
| pGE2134 | 308-406 | 437-611 |
| pGE1134 | 121-406 | 437-611 |
| pGE5634 | 1-406 | 437-611 |
| pGE271 | 1-119 | 437-611 |

TABLE 7-continued

Plasmids for expression of Gag-Env fusion proteins

| Plasmid | Product: Gag protein region (a.a.) | Product: Env protein region (a.a.) |
|---|---|---|
| pGE2112 | 308-406 | 437-722 |
| pGE1112 | 121-406 | 437-722 |
| pGE5612 | 1-406 | 437-722 |
| pGE2142 | 308-406 | 437-826 |
| pGE1142 | 121-406 | 437-826 |
| pGE5642 | 1-406 | 437-826 |
| pGE30 | 308-436 | 437-826 |
| PGE33 | 308-406 | 512-611 |
| PGE1133 | 121-406 | 512-611 |
| pGE5633 | 1-406 | 512-611 |
| pGE281 | 1-119 | 512-611 |
| pGE31 | 308-437 | 512-611 |
| pGE218 | 308-406 | 512-699 |
| pGE118 | 121-406 | 512-699 |
| pGE280 | 1-119 | 512-699 |
| pGE34 | 308-406 | 721-826 |
| pGE1145 | 121-406 | 721-826 |
| pGE5645 | 1-406 | 721-826 |
| pGE290 | 1-119 | 721-826 |
| pGE32 | 308-435 | 723-826 |

TABLE 8

Western blotting of Gag-Env fusion protein with sera of HIV-1 carriers

| Antigen | Sera | + | ± | − | Total |
|---|---|---|---|---|---|
| Gag (308-406)-Env (512-611) | AC | 36 | − | − | 36 |
| | ARC | 1 | − | − | 1 |
| | AIDS | 4 | − | − | 4 |

TABLE 9

Reactivity of the purified Gag-Env fusion protein with sera of HIV-1 carriers and non-infected persons

| Sera | − | + | ++ | +++ | Total |
|---|---|---|---|---|---|
| AC | 0 | 1 | 1 | 53 | 55 |
| ARC | 0 | 0 | 0 | 1 | 1 |
| AIDS | 0 | 0 | 0 | 4 | 4 |
| Non-infected individuals (healthy individuals) | 84 | 0 | 0 | 0 | 84 |

−: No reaction takes place with 320 ng of a purified fusion protein.
+, ++, +++: Reaction takes place with at least 20 ng, at least 10 ng, and at least 5 ng of the purified fusion protein.

TABLE 10

Reactivity of the Gag proteins with serum antibodies of HIV-1 carriers

| Sera | Reacted with at least 320 | 160 | 80 | 40 | 20 | 10 | 5 (ng) | Reacted | Tested |
|---|---|---|---|---|---|---|---|---|---|
| (A) Detection of anti-p55 antibodies in the sera from HIV-1 carriers | | | | | | | | | |
| AC | | | | 3 | 2 | 3 | 27 | 35 | 35 |
| ARC | | | | | | 1 | | 1 | 1 |
| AIDS | | | | | | 3 | 1 | 4 | 4 |
| (B) Detection of anti-p17 antibodies in the sera from HIV-1 carriers | | | | | | | | | |
| AC | 1 | 5 | 3 | 8 | 11 | 5 | | 33 | 35 |
| ARC | | | | 1 | | | | 1 | 1 |
| AIDS | | 2 | | 1 | | | | 3 | 4 |
| (C) Detection of anti-p24 antibodies in the sera from HIV-1 carriers | | | | | | | | | |
| AC | 4 | 2 | 4 | 6 | 9 | 3 | 3 | 31 | 35 |
| ARC | | | | | | | | 0 | 1 |
| AIDS | 1 | 1 | 2 | | | | | 4 | 4 |
| (D) Detection of anti-p15 antibodies in the sera from HIV-1 carriers | | | | | | | | | |
| AC | 1 | 2 | 8 | 16 | 3 | | | 30 | 35 |
| ARC | | | | 1 | | | | 1 | 1 |
| AIDS | | | 1 | 2 | | | | 3 | 4 |

What is claimed is:

1. An HIV-1 Gag-Env fusion protein consisting of amino acids 308–406 of the Gag protein of SEQ. ID. NO. 1 and amino acids 512–611 of the Env protein of SEQ. ID. NO. 2, wherein the amino terminus of the Env peptide is fused to the carboxyl terminus of the Gag peptide.

2. An HIV-1 Gag-Env fusion protein consisting of amino acids 121–406 of the Gag protein of SEQ. ID. NO. 1 and amino acids 512–611 of the Env protein of SEQ. ID. NO. 2, wherein the amino terminus of the Env peptide is fused to the carboxyl terminus of the Gag peptide.

3. A composition containing the HIV-1 Gag-Env fusion protein of either claims 1 or 2 and an HIV-1 Gag protein consisting of amino acids 1–500 of SEQ. ID. NO. 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 500 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: Human immunodeficiency virus type 1

( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Gly | Ala | Arg | Ala | Ser | Val | Leu | Ser | Gly | Gly | Glu | Leu | Asp | Lys | Trp |
| 1 | | | | 5 | | | | | 10 | | | | | 15 | |
| Glu | Lys | Ile | Arg | Leu | Arg | Pro | Gly | Gly | Lys | Lys | Gln | Tyr | Lys | Leu | Lys |
| | | | 20 | | | | | 25 | | | | | 30 | | |
| His | Ile | Val | Trp | Ala | Ser | Arg | Glu | Leu | Glu | Arg | Phe | Ala | Val | Asn | Pro |
| | | 35 | | | | | 40 | | | | | 45 | | | |
| Gly | Leu | Leu | Glu | Thr | Ser | Glu | Gly | Cys | Arg | Gln | Ile | Leu | Gly | Gln | Leu |
| | 50 | | | | | 55 | | | | | 60 | | | | |
| Gln | Pro | Ser | Leu | Gln | Thr | Gly | Ser | Glu | Glu | Leu | Arg | Ser | Leu | Tyr | Asn |
| 65 | | | | | 70 | | | | | 75 | | | | | 80 |
| Thr | Ile | Ala | Val | Leu | Tyr | Cys | Val | His | Gln | Arg | Ile | Asp | Val | Lys | Asp |
| | | | | 85 | | | | | 90 | | | | | 95 | |
| Thr | Lys | Glu | Ala | Leu | Asp | Lys | Ile | Glu | Glu | Glu | Gln | Asn | Lys | Ser | Lys |
| | | | 100 | | | | | 105 | | | | | 110 | | |
| Lys | Lys | Ala | Gln | Gln | Ala | Ala | Ala | Asp | Thr | Gly | Asn | Asn | Ser | Gln | Val |
| | | 115 | | | | | 120 | | | | | 125 | | | |
| Ser | Gln | Asn | Tyr | Pro | Ile | Val | Gln | Asn | Leu | Gln | Gly | Gln | Met | Val | His |
| | 130 | | | | | 135 | | | | | 140 | | | | |
| Gln | Ala | Ile | Ser | Pro | Arg | Thr | Leu | Asn | Ala | Trp | Val | Lys | Val | Val | Glu |
| 145 | | | | | 150 | | | | | 155 | | | | | 160 |
| Glu | Lys | Ala | Phe | Ser | Pro | Glu | Val | Ile | Pro | Met | Phe | Ser | Ala | Leu | Ser |
| | | | | 165 | | | | | 170 | | | | | 175 | |
| Glu | Gly | Ala | Thr | Pro | Gln | Asp | Leu | Asn | Thr | Met | Leu | Asn | Thr | Val | Gly |
| | | | 180 | | | | | 185 | | | | | 190 | | |
| Gly | His | Gln | Ala | Ala | Met | Gln | Met | Leu | Lys | Glu | Thr | Ile | Asn | Glu | Glu |
| | | 195 | | | | | 200 | | | | | 205 | | | |
| Ala | Ala | Glu | Trp | Asp | Arg | Leu | His | Pro | Val | His | Ala | Gly | Pro | Ile | Ala |
| | 210 | | | | | 215 | | | | | 220 | | | | |
| Pro | Gly | Gln | Met | Arg | Glu | Pro | Arg | Gly | Ser | Asp | Ile | Ala | Gly | Thr | Thr |
| 225 | | | | | 230 | | | | | 235 | | | | | 240 |
| Ser | Thr | Leu | Gln | Glu | Gln | Ile | Gly | Trp | Met | Thr | His | Asn | Pro | Pro | Ile |
| | | | | 245 | | | | | 250 | | | | | 255 | |
| Pro | Val | Gly | Glu | Ile | Tyr | Lys | Arg | Trp | Ile | Ile | Leu | Gly | Leu | Asn | Lys |
| | | | 260 | | | | | 265 | | | | | 270 | | |
| Ile | Val | Arg | Met | Tyr | Ser | Pro | Thr | Ser | Ile | Leu | Asp | Ile | Arg | Gln | Gly |
| | | 275 | | | | | 280 | | | | | 285 | | | |

-continued

```
Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500
```

( 2 ) INFORMATION FOR SEQ ID NO:2:

( i ) SEQUENCE CHARACTERISTICS:
( A ) LENGTH: 826 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Ser Ala Thr Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Val Val Leu Val Asn Val Thr Glu Asn
    50                  55                  60

Phe Asn Met Trp Lys Asn Asp Met Val Glu Gln Met His Glu Asp Ile
65                  70                  75                  80

Ile Ser Leu Trp Asp Gln Ser Leu Lys Pro Cys Val Lys Leu Thr Pro
                85                  90                  95

Leu Cys Val Ser Leu Lys Cys Thr Asp Leu Lys Asn Asp Thr Asn Thr
            100                 105                 110
```

-continued

| | | | | | | | | | | | | | | | |
|---|---|---|---|---|---|---|---|---|---|---|---|---|---|---|---|
| Asn | Ser | Ser | Ser | Gly | Arg | Met | Ile | Met | Glu | Lys | Gly | Glu | Ile | Lys | Asn |
| | | 115 | | | | | 120 | | | | | 125 | | | |
| Cys | Ser | Phe | Asn | Ile | Ser | Thr | Ser | Ile | Arg | Asp | Lys | Val | Gln | Lys | Glu |
| | 130 | | | | | 135 | | | | | 140 | | | | |
| Tyr | Ala | Phe | Phe | Tyr | Lys | Leu | Asp | Ile | Val | Pro | Ile | Asp | Asn | Thr | Ser |
| 145 | | | | | 150 | | | | | 155 | | | | | 160 |
| Tyr | Arg | Leu | Ile | Ser | Cys | Asn | Thr | Ser | Val | Ile | Thr | Gln | Ala | Cys | Pro |
| | | | | 165 | | | | | 170 | | | | | 175 | |
| Lys | Val | Ser | Phe | Glu | Pro | Ile | Pro | Ile | His | Tyr | Cys | Ala | Pro | Ala | Gly |
| | | | 180 | | | | | 185 | | | | | 190 | | |
| Phe | Ala | Ile | Leu | Lys | Cys | Asn | Asn | Lys | Thr | Phe | Asn | Gly | Thr | Gly | Pro |
| | | 195 | | | | | 200 | | | | | 205 | | | |
| Cys | Thr | Asn | Val | Ser | Thr | Val | Gln | Cys | Thr | His | Gly | Ile | Arg | Pro | Val |
| | 210 | | | | | 215 | | | | | 220 | | | | |
| Val | Ser | Thr | Gln | Leu | Leu | Leu | Asn | Gly | Ser | Leu | Ala | Glu | Glu | Asp | Val |
| 225 | | | | | 230 | | | | | 235 | | | | | 240 |
| Val | Ile | Arg | Ser | Ala | Asn | Phe | Thr | Asp | Asn | Ala | Lys | Thr | Ile | Ile | Val |
| | | | | 245 | | | | | 250 | | | | | 255 | |
| Gln | Leu | Asn | Thr | Ser | Val | Glu | Ile | Asn | Cys | Thr | Arg | Pro | Asn | Asn | Asn |
| | | | 260 | | | | | 265 | | | | | 270 | | |
| Thr | Arg | Lys | Ser | Ile | Arg | Ile | Gln | Arg | Gly | Pro | Gly | Arg | Ala | Phe | Val |
| | | 275 | | | | | 280 | | | | | 285 | | | |
| Thr | Ile | Gly | Lys | Ile | Gly | Asn | Met | Arg | Gln | Ala | His | Cys | Asn | Ile | Ser |
| | 290 | | | | | 295 | | | | | 300 | | | | |
| Arg | Ala | Lys | Trp | Asn | Ala | Thr | Leu | Lys | Gln | Ile | Ala | Ser | Lys | Leu | Arg |
| 305 | | | | | 310 | | | | | 315 | | | | | 320 |
| Glu | Gln | Phe | Gly | Asn | Asn | Lys | Thr | Ile | Ile | Phe | Lys | Gln | Ser | Ser | Gly |
| | | | | 325 | | | | | 330 | | | | | 335 | |
| Gly | Asp | Pro | Glu | Ile | Val | Thr | His | Ser | Phe | Asn | Cys | Gly | Gly | Glu | Phe |
| | | | 340 | | | | | 345 | | | | | 350 | | |
| Phe | Tyr | Cys | Asn | Ser | Thr | Gln | Leu | Phe | Asn | Ser | Thr | Trp | Phe | Asn | Ser |
| | | 355 | | | | | 360 | | | | | 365 | | | |
| Thr | Trp | Ser | Thr | Glu | Gly | Ser | Asn | Asn | Thr | Glu | Gly | Ser | Asp | Thr | Ile |
| | 370 | | | | | 375 | | | | | 380 | | | | |
| Thr | Leu | Pro | Cys | Arg | Ile | Lys | Gln | Phe | Ile | Asn | Met | Trp | Gln | Glu | Val |
| 385 | | | | | 390 | | | | | 395 | | | | | 400 |
| Gly | Lys | Ala | Met | Tyr | Ala | Pro | Pro | Ile | Ser | Gly | Gln | Ile | Arg | Cys | Ser |
| | | | | 405 | | | | | 410 | | | | | 415 | |
| Ser | Asn | Ile | Thr | Gly | Leu | Leu | Leu | Thr | Arg | Asp | Gly | Gly | Asn | Asn | Asn |
| | | | 420 | | | | | 425 | | | | | 430 | | |
| Asn | Gly | Ser | Glu | Ile | Phe | Arg | Pro | Gly | Gly | Gly | Asp | Met | Arg | Asp | Asn |
| | | 435 | | | | | 440 | | | | | 445 | | | |
| Trp | Arg | Ser | Glu | Leu | Tyr | Lys | Tyr | Lys | Val | Val | Lys | Ile | Glu | Pro | Leu |
| | 450 | | | | | 455 | | | | | 460 | | | | |
| Gly | Val | Ala | Pro | Thr | Lys | Ala | Lys | Arg | Arg | Val | Val | Gln | Arg | Glu | Lys |
| 465 | | | | | 470 | | | | | 475 | | | | | 480 |
| Arg | Ala | Val | Gly | Ile | Gly | Ala | Leu | Phe | Leu | Gly | Phe | Leu | Gly | Ala | Ala |
| | | | | 485 | | | | | 490 | | | | | 495 | |
| Gly | Ser | Thr | Met | Gly | Cys | Thr | Ser | Met | Thr | Leu | Thr | Val | Gln | Ala | Arg |
| | | | 500 | | | | | 505 | | | | | 510 | | |
| Gln | Leu | Leu | Ser | Asp | Ile | Val | Gln | Gln | Gln | Asn | Asn | Leu | Leu | Arg | Ala |
| | | 515 | | | | | 520 | | | | | 525 | | | |
| Ile | Glu | Ala | Gln | Gln | His | Leu | Leu | Gln | Leu | Thr | Val | Trp | Gly | Ile | Lys |

-continued

```
          530                                     535                                     540

Gln Leu Gln Ala Arg Ile Leu Ala Val Glu Arg Tyr Leu Lys Asp Gln
545                 550                 555                 560

Gln Leu Leu Gly Ile Trp Gly Cys Ser Gly Lys Leu Ile Cys Thr Thr
                565                 570                 575

Ala Val Pro Trp Asn Ala Ser Trp Ser Asn Lys Ser Leu Glu Gln Ile
            580                 585                 590

Trp Asn Asn Met Thr Trp Met Glu Trp Asp Arg Glu Ile Asn Asn Tyr
        595                 600                 605

Thr Ser Leu Ile His Ser Leu Ile Glu Glu Ser Gln Asn Gln Gln Glu
    610                 615                 620

Lys Asn Glu Gln Glu Leu Leu Glu Leu Asp Lys Trp Ala Ser Leu Trp
625                 630                 635                 640

Asn Trp Phe Asn Ile Thr Asn Trp Leu Trp Tyr Ile Lys Leu Phe Ile
                645                 650                 655

Met Ile Val Gly Gly Leu Val Gly Leu Arg Ile Val Phe Ala Val Leu
            660                 665                 670

Ser Ile Val Asn Arg Val Arg Gln Gly Tyr Ser Pro Leu Ser Phe Gln
        675                 680                 685

Thr His Leu Pro Ile Pro Arg Gly Pro Asp Arg Pro Glu Gly Ile Glu
    690                 695                 700

Glu Glu Gly Gly Glu Arg Asp Arg Asp Arg Ser Ile Arg Leu Val Asn
705                 710                 715                 720

Gly Ser Leu Ala Leu Ile Trp Asp Asp Leu Arg Ser Leu Cys Leu Phe
                725                 730                 735

Ser Tyr His Arg Leu Arg Asp Leu Leu Leu Ile Val Thr Arg Ile Val
            740                 745                 750

Glu Leu Leu Gly Arg Arg Gly Trp Glu Ala Leu Lys Tyr Trp Trp Asn
        755                 760                 765

Leu Leu Gln Tyr Trp Ser Gln Glu Leu Lys Asn Ser Ala Val Asn Leu
    770                 775                 780

Leu Asn Ala Thr Ala Ile Ala Val Ala Glu Gly Thr Asp Arg Val Ile
785                 790                 795                 800

Glu Val Leu Gln Ala Ala Tyr Arg Ala Ile Arg His Ile Pro Arg Arg
                805                 810                 815

Ile Arg Gln Gly Leu Glu Arg Ile Leu Leu
            820                 825
```

( 2 ) INFORMATION FOR SEQ ID NO:3:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:3:

TATGGCTAAG 10

( 2 ) INFORMATION FOR SEQ ID NO:4:

( i ) SEQUENCE CHARACTERISTICS:
( A ) LENGTH: 12 base pairs
( B ) TYPE: nucleic acid
( C ) STRANDEDNESS: single -continued ( D ) TOPOLOGY: lincar ( i i i ) HYPOTHETICAL: NO ( i v ) ANTI-SENSE: NO ( x i ) SEQUENCE DESCRIPTION: SEQ ID NO:4:

AATTCTTAGC CA 12